US006140137A

United States Patent [19]
Sigler et al.

[11] Patent Number: 6,140,137
[45] Date of Patent: Oct. 31, 2000

[54] CONJUGATES AND SPECIFIC IMMUNOASSAYS FOR THE METHADONE METABOLITE 2-ETHYLIDENE-1,5-DIMETHYL-3,3-DIPHENYLPYRROLIDINE

[75] Inventors: Gerald F. Sigler, Carmel, Ind.; Michael J. Powell, Danville, Calif.; William A. Coty, Livermore, Calif.; Anthony J. Sanchez, Concord, Calif.

[73] Assignee: Microgenics Corporation, Fremont, Calif.

[21] Appl. No.: 08/930,959

[22] PCT Filed: Sep. 24, 1997

[86] PCT No.: PCT/US97/17784

§ 371 Date: Sep. 24, 1997

§ 102(e) Date: Sep. 24, 1997

[87] PCT Pub. No.: WO98/54133

PCT Pub. Date: Dec. 3, 1998

Related U.S. Application Data

[60] Provisional application No. 60/047,773, May 27, 1997.
[51] Int. Cl.$^7$ .................... G01N 33/536; C07K 16/44; C12N 9/96
[52] U.S. Cl. .................... 436/536; 435/7.9; 435/7.93; 435/7.94; 435/188; 436/815; 530/388.9; 530/389.8; 530/403; 530/405
[58] Field of Search .................... 435/7.9, 188, 7.93, 435/7.94; 530/388.9, 389.8, 403, 405; 436/815, 536

[56] References Cited

U.S. PATENT DOCUMENTS

| | | | |
|---|---|---|---|
| 4,104,367 | 8/1978 | Gomez et al. | |
| 4,708,929 | 11/1987 | Henderson | 436/537 |
| 5,073,629 | 12/1991 | Dubler et al. | 436/536 |
| 5,254,677 | 10/1993 | Guder et al. | 435/18 |
| 5,439,798 | 8/1995 | Sigler et al. | 436/545 |
| 5,444,161 | 8/1995 | Manning et al. | 536/4.1 |
| 5,464,747 | 11/1995 | Eisenbeis et al. | 435/7.6 |
| 5,514,560 | 5/1996 | Manning et al. | 435/7.4 |
| 5,518,887 | 5/1996 | Parsons et al. | 435/7.1 |
| 5,525,474 | 6/1996 | Sigler et al. | 435/7.7 |
| 5,710,256 | 1/1998 | Buechler | 530/388.9 |

FOREIGN PATENT DOCUMENTS

| | | |
|---|---|---|
| 0413561 | 11/1996 | European Pat. Off. |
| WO 90/15798 | 12/1990 | WIPO |
| WO 95/16894 | 6/1995 | WIPO |
| WO 95/20763 | 8/1995 | WIPO |
| WO 96/31496 | 10/1996 | WIPO |

OTHER PUBLICATIONS

L. DeCato et al, Clinical Immunology and Immunopathology, vol. 9, pp. 293–300, 1978.

Abbott et al., "Methadone metabolism in the rat in vivo: identification of a novel formamide metabolite" *Xenobotica* (1985) 15(2):129–140.

Axelrod, "The enzymatic N–demethylation of narcotic drugs" *National Institute of Mental Health, National Institutes of Health, Public Health Service, U.S. Department of Health, Education, and Welfare,* Bethesda, Maryland, (Mar. 16, 1956) pp. 322–330.

Baugh et al., "Simultaneous gas chromatography/mass spectrometry assay of methadone and 2–ethyl–1, 5–dimethyl–3, 3–diphenylpyrrolidine (EDDP) in urine" *J. Forensic Sciences* (1991) 36(2):548–555.

Beckett et al., "The biotransformation of methadone in man: synthesis and identification of a major metabolite" *J. Pharm. Pharmac.* (1968) 20:754–762.

Brine et al., "p–hydroxymethadone: synthesis, crystal structure and CD properties" *J. Chem. Soc. Perkin Trans.* (1991) 1:1809–1814.

Brine et al., "Synthesis and spectral properties of optically active 2–ethylidene–1, 5–dimethyl–3, 3–diphenylpyrrolidine: primary methadone metabolite" *J. Heterocyclic Chem.* (1986) 23:369–374.

Brinkley et al., "A brief survey of methods for preparing protein conjugates with dyes, haptens, and cross–linking reagents" *Bioconjugate Chem.* (1992) 3:2–13.

Brown et al., "Chemical modification of lactose repressor protein using N–substituted maleimides" *J. Biol. Chem.* (1979) 254(12):5128–5134.

Budd et al., "Thin–layer chromatographic screening and confirmation of methadone and its primary metabolite in urine" *Clinical Toxicology* (1980) 16(1):55–59.

Furness et al., "The determination of methadone and metabolites in human urine by HPLC with ultraviolet, and particle beam mass spectrometric detection" *J. Liquid Chromatography* (1994) 17(20):4431–4444.

Gerber et al., "The metabolism of d–, l and dl–methadone in the isolated perfused rat liver" *J. Pharmacol. Experimental Therapeutics* (1977) 200(3):487–495.

Henderson, "CEDIA™, a new homogenous immunoassay system" *Clin. Chem.* (1986) 32(9):1637–1641.

Jain et al., "A comparison of methods used in the detection of methadone and its primary metabolite" *J. Analytical Toxicology* (1977) 1:6–9.

Lynn et al., "Identification of glucuronide metabolites and d–and l–methadone in bile from the isolated perfused rat liver" *Res. Comm. Chem. Pathol. Pharmacol.* (1976) 15(1):1–10.

(List continued on next page.)

*Primary Examiner*—Mary E. Ceperley
*Attorney, Agent, or Firm*—Wood, Herron & Evans, L.L.P.

[57] ABSTRACT

Novel chemical analogs of the methadone metabolite 2-ethylidene-1,5-dimethyl-3,3-diphenylpyrrolidine (EDDP) are disclosed. The derivatives can be used for formation of EDDP-protein conjugates. The conjugates can be used in turn to raise antibodies reactive with EDDP and having a low cross-reactivity with methadone. The antibodies and EDDP-enzyme polypeptide conjugates provide the basis for specific immunoassays used in monitoring compliance with methadone treatment.

35 Claims, 7 Drawing Sheets

OTHER PUBLICATIONS

Nicar et al., "Monitoring compliance in methadone therapy" *Clin. Chem.* (1996) 42(6):S226 (Abstract 543).

Pohland et al., "Synthesis and identification of metabolites resulting from the biotransformation of DL–methadone in man and in the rat" *J. Medicinal Chem.* (1971) 14(3):194–197.

Product Insert kit from Diagnostic Reagents, Inc., "Drugs of Abuse Urine Calibrators A and Controls A" (1993), 1 page total.

Product Insert kit from Diagnostic Reagents, Inc., "Drugs of Abuse Urine Calibrators" (1992), 1 page total.

Product Insert kit from Diagnostic Reagents, Inc., "Methadone Metabolite Enzyme Immunoassay" (1993), 2 pages total.

Smyth et al., "Reactions of N–ethylmaleimide with peptides and amino acids" *Biochem J.* (1964) 91:589–595.

Sullivan et al., "Metabolism of d–methadone: isolation and identification of analgesically active metabolites" *Life Sciences* (1972) 11(Part I):1093–1104.

Sullivan et al., "The identification of three new metabolites of methadone in man and in the rat" *J. Amer. Chem. Soc.* (1972) 94(11):4050–4051.

Sullivan et al., "Urinary metabolites of dl–methadone in maintenance subjects" *J. Medicinal Chem.* (1973) 16(8):909–913.

Sung et al., "The metabolic fate of the optical isomers of methadone" *Department of Pharmacology, School of Medicine and the College of Pharmacy, University of California,* San Francisco, California (Jun. 15, 1953) pp. 244–254.

CONJUGATES AND SPECIFIC IMMUNOASSAYS FOR THE METHADONE METABOLITE 2-ETHYLIDENE-1,5-DIMETHYL-3,3-DIPHENYLPYRROLIDINE

REFERENCE TO RELATED APPLICATIONS

This is a national stage application under 35 USC § 371 of an International application filed on the same date. This application claims the priority benefit of U.S. Provisional Application U.S. 60/047,773, filed on May 27, 1997.

TECHNICAL FIELD

This invention relates generally to the field of the detection of drug metabolites in biological samples. More specifically, it provides a system for developing hapten conjugates and specific antibodies for use in assay systems for detection or quantitation of the title methadone metabolite.

BACKGROUND ART

Methadone has been widely used as an aid in withdrawal from heroin addiction. Compliance with methadone therapy is frequently monitored by analysis of urine samples for the presence of methadone, which can be performed using one of several commercially available immunoassays for methadone.

However, there are several occasions when a simple assay for methadone provides in incorrect or incomplete diagnostic information. For example, the methadone may be so extensively metabolized that the concentration excreted falls below that of the assay being used. To the extent that the assay distinguishes between methadone and excreted metabolites, the test can be negative even for a patient in full compliance with therapy (Nicar et al., Clin. Chem. 42:543, 1996). In another example, a patient may add methadone to their sample to disguise the fact that they are not adhering to the treatment protocol. Samples that have been tampered with can in principle be distinguished in that they will not contain filterable metabolites of methadone that are also present in urine when the methadone treatment protocol is being properly adhered to.

Both these types of situations could be easily recognized if it were possible to independently measure the presence of the excreted metabolite. In practical terms, detecting methadone metabolites is difficult because of the chemical and immunological similarity with methadone itself. Accordingly, there is a need for reagents and techniques that would permit routine monitoring of methadone metabolites in a clinical setting.

A major pathway of metabolism of methadone is dem-ethylation to the presumed intermediate N-desmethylmethadone, leading to urinary excretion of 2-ethylidene-1,5-dimethyl-3,3-diphenylpyrrolidine herein abbreviated as EDDP), 2-ethyl-5-methyl-3,3-diphenyl-1-pyrroline (EMDP), and their ring-hydroxylated analogs (Sullivan et al., J. Medicinal Chem. 16:909, 1973). These structures are depicted in FIG. 1. Lesser amounts of 4-dimethylamino-2,2-diphenylvaleric acid (formed by side-chain oxidation); 1,5-dimethyl-3,3-diphenyl-2-pyrrolidone (resulting from subsequent N-demethylation and cyclization), ring-hydroxylated methadone, and normethadol are also found. Methadone N-oxide is formed by storage of samples at 30° C. In human volunteers receiving~100 mg of dl-methadone orally, EDDP was found by Sullivan et al. to be the most prominent metabolite in urine, present at a level roughly comparable with that of methadone itself.

In order to detect methadone metabolites, Sullivan et al. extracted urine with methylene chloride, hydrolyzed the reconstituted extract using β-glucuronidase and aryl sulfatase, optionally acetylated or methylated the product, and then characterized it by gas chromatography or combined gas chromatography-mass spectroscopy.

The synthesis and spectral properties of optically active EDDP were described by Brine et al. (J. Heterocyclic Chem., 23:369, 1986). The $^1$H—NMR analysis suggested that the free base exists predominantly in an enamine form. CD and ORD studies provided data consistent with a fairly rigid enamine structure.

Simultaneous gas chromatography mass spectrometry (GC/MS) assay for EDDP in urine was described by Baugh et al. (J. Forensic Sci. 36:548, 1991). Urine was extracted with 1-chlorobutane at pH~9, the organic phase was back-extracted into acetate buffer, adjusted to pH~9, and re-extracted with I -chlorobutane. Area corresponding to ions at m/z 277, 262, and 276 was measured. Quantitation was enhanced by using deuterated methadone as the internal standard. Although the assay is quantitative, it relies on a multi-step extraction procedure and the availability of equipment to perform GC/MS.

Thin-layer chromatography (TLC) screening of methadone and EDDP in urine was described by Budd et al. (Clin. Toxicol. 16:55, 1980). Metabolites were extracted into an organic solvent, and then chromatographed in ethyl acetate-:methanol:diethylamine or ethyl acetate:methylene choride:propylamine. Dried plates were developed using acidified iodoplatinate reagent. Although this permits a number of samples to be processed in the same day, this type of assay is non-quantitative and subject to variations in solvent mixtures.

More suited for routine clinical analysis are immunoassays, in which a specific antibody is used to distinguish and quantify an analyte of interest in a biological sample. The general art of immunoassay and its use in clinical monitoring is well known. Assays for analytes of the size of EDDP are often competition assays. Immunoassays typically involve either the specific isolation of the analyte from the sample mediated by antibody, or the formation of analyte-antibody complexes in situ (a "homogeneous" assay system). In either case, formation of an analyte-antibody complex ultimately leads to a signal which is directly or inversely related to the amount of analyte present in the original sample.

A particularly powerful homogeneous assay system is the cloned enzyme donor immunoassay (CEDIA®), described in U.S. Pat. No. 4,708,929, and in Henderson, Clin. Chem. 32:1637, 1986. In a preferred form of the CEDIA® assay, two subunits of the enzyme β-galactosidase associate to provide the detectable signal, which is quantitatively affected by analyte-specific antibody except in the presence of a sample containing free analyte.

All specific immunoassays require the availability of an antibody that binds the analyte of interest but not potential interfering substances. An immunoassay for EDDP capable of differentiating samples spiked with methadone requires an antibody with a very high relative affinity for EDDP in relation to methadone.

A commercial assay for EDDP is marketed by Diagnostic Reagents, Inc. of Mountain View, Calif. This is a homogeneous enzyme immunoassay based on the binding of an anti-EDDP antibody with a glucose-6-phosphate dehydrogenase drug conjugate, which inhibits the activity of the enzyme. Presence of sample analyte in the reaction mixture binds the antibody and increases enzyme activity. The utility of this assay is limited by its specificity. EDDP gives a positive result at 300 ng/mL, EMDP at 400 ng/mL, and methadone itself at 5000 ng/mL. In other words, the assay when used alone is unable to distinguish between a sample containing EDDP, and another sample spiked with methadone at a somewhat higher level.

The limited specificity in current art EDDP assays is attributable to the limited specificity in the antibody in the assay. This in turn is attributable to the unsuitability of current art immunogens for generating antibodies with better specificity.

DISCLOSURE OF THE INVENTION

The present invention provides a system for the improved detection of EDDP in biological samples. New chemical analogs of EDDP are described that permit EDDP to be linked to an immunogenic carrier. In turn, the immunogens can be used reproducibly to generate antibodies with an exquisite ability to distinguish EDDP from methadone, EMDP, and other potential interfering substances. The specific antibodies obtained can be used in any suitable immunoassay format for the detection or quantitation of EDDP in a sample, distinct from any methadone that is present. Chemical derivatives of EDDP according to this invention can also be conjugated to proteins or surfaces as a competitive target for the antibody in an immunoassay.

Certain embodiments of this invention relate to a purified or synthetic compound of the formula:

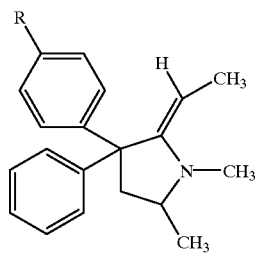

and salts thereof, wherein R is a substituent containing at least one C atom. In certain embodiments, R comprises a polyamino acid. In certain embodiments, R is of the structure Y—R$^1$—O—, wherein R$^1$ is a hydrocarbyl diradical having 1–10 carbon atoms and Y is selected from the group consisting of:

—COOH;

—COOR$^2$; wherein R$^2$ is a hydrocarbyl radical having 1–20 carbon atoms;

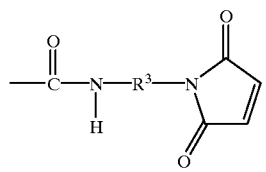

wherein R$^3$ is a hydrocarbyl diradical having 1–20 carbon atoms; and

—CO—L—Q, wherein Q is a poly(amino acid) and L is a bond or a diradical linker group, such as

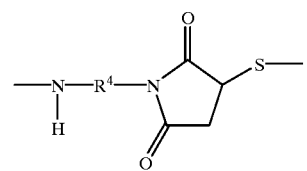

wherein R$^4$ is a hydrocarbyl diradical of 1–20 carbon atoms.

Where present, the polyamino acid may be an immunogenic peptide, an enzyme, or an enzyme donor polypeptide.

Additional embodiments of this invention relate to synthetic methods for preparing the chemical compounds and EDDP-protein conjugates outlined above, comprising synthesizing the intermediate 2-ethyl-1,5-dimethyl-3-p-hydroxyphenyl-3-phenylpyrroline (p—HO—EDDP) or the intermediate 1,5-dimethyl-3-(p-alkoxyphenyl)-3-phenyl-2-pyrrolidone. Other embodiments relate to methods for preparing EDDP-protein conjugates comprising synthesizing an EDDP derivative of this invention with a suitable reactive group for protein conjugation.

Also embodied in this invention are monoclonal and polyclonal antibodies raised against any of the compounds outlined above and specific for the compound 2-ethylidene-1,5-dimethyl-3,3-diphenylpyrrolidone (EDDP). Also embodied is an antibody specific for EDDP and having a low level of cross-reactivity with methadone or with the metabolite 2-ethyl- 5-methyl-3,3-diphenyl-1-pyrroline (EMDP). Also embodied are methods for raising such antibodies by stimulating an immunocompetent animal, cell or viral particle with an immunogenic EDDP-protein conjugate of this invention or using an EDDP-protein conjugate to select a hybridoma of the desired specificity.

Also embodied in this invention are EDDP-protein conjugates for conducting a competitive assay for EDDP in a sample, wherein the protein is either coupled to a solid support or capable of generating a detectable signal. The signal may be generated by a radioisotope, fluorochrome or other signal-generating or quenching system attached to the protein (or by an adaptation that allows the signal-generating or quenching system to be subsequently attached), or the protein may be an enzyme or enzyme component capable of assembling into an active enzyme in the presence or absence of EDDP in the sample.

Further embodiments of this invention relate to methods for detecting EDDP in a sample, exemplified by but not limited to a urine sample, comprising combining the sample with the an anti-EDDP antibody of this invention under conditions that permit formation of a stable EDDP-antibody complex; and detecting or quantitating any complex formed. Other embodiments relate to methods for detecting EDDP in a sample by competition with an EDDP-protein conjugate. Preferred methods are methods using an enzyme to produce a detectable signal, and homogeneous assay methods such as a cloned enzyme donor immunoassay. Any EDDP detected in a sample may be correlated with administration of methadone to a subject, particularly a human on methadone therapy.

Additional embodiments relate to certain reagents embodied in this invention, reagent combinations, and kits for performing an assay method for EDDP in a biological sample.

BEST MODE FOR CARRYING OUT THE INVENTION

The present invention is focused on the preparation of analogs of the methadone metabolite EDDP, which can then be used for preparing immunogens and enzyme conjugates useful in the development of immunoassays for the measurement of EDDP.

Upon facing the challenge of developing EDDP conjugates, a typical synthetic approach is to derivatize from the N residue in the pyrrolidone ring. EMDP, which lacks the N-methyl group of EDDP, is commercially available and a suitable starting compound. The C=N double bond is reduced to yield the secondary amine, which can then be attached to a linking group.

Figure 1:
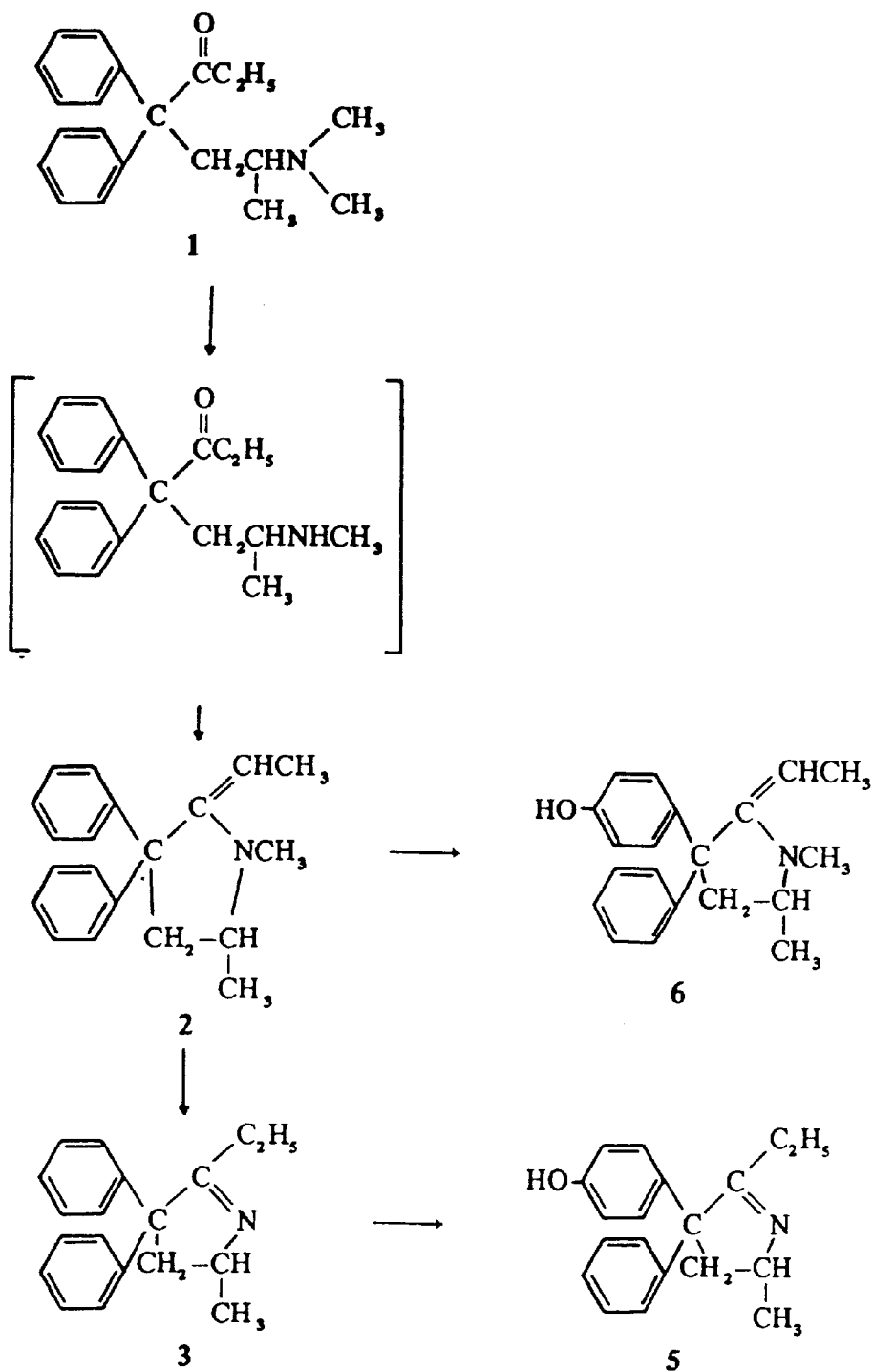
FIG. 1 is a chemical scheme showing urinary metabolites in subjects on methadone maintenance. Methadone (Structure 1) is metabolized through a presumed intermediate to the major metabolite EDDP (Structure 2) and the minor metabolite EMDP (Structure 3), which may be ring-hydroxylated to Structures 6 and 5, respectively. This scheme is adapted from Sullivan et al. (supra).
Figure 2:
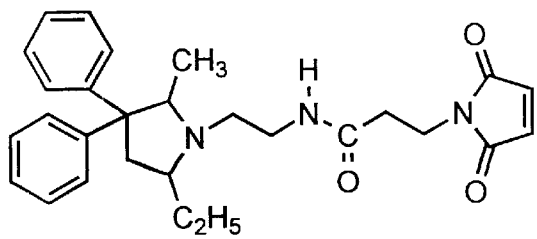
FIG. 2 is a drawing of an EDDP analog designated EMDP—MPS. This analog was obtained by derivatizing the N in the heterocyclic ring of EMDP. Antibodies raised using EDDP-protein conjugates based on this analog generally had an unsatisfactory degree of cross-reactivity with methadone.

This approach was adopted in a preliminary series of experiments. The EDDP analog EMDP—MPS with the structure shown in FIG. 2 was synthesized and conjugated to KLH that has been thiolated using 2-iminothiolane. The hapten-protein conjugate was used as an immunogen to prepare monoclonal antibodies. Five separate fusions were performed using immunocytes from hyperimmunized mice. The monoclonal antibodies obtained had a cross-reactivity with methadone of 0.8 to 5.6% and a cross-reactivity with EMDP of 1.0–6.8%.

With a view to obtaining antibodies with improved ability to discriminate between these structures, an entirely different synthetic approach was developed. A novel family of EDDP analogs was obtained by conjugating from the para position of a phenyl group of EDDP. To accomplish this, a synthetic method was developed for the preparation of para-hydroxylated EDDP, 1,5-Dimethyl-3-(p-hydroxyphenyl)-3-phenyl-2-pyrrolidone (abbreviated herein as p—HO—EDDP). This structure has previously been identified as yet another methadone metabolite, but has not previously been synthesized. p—HO—EDDP was then alkylated to yield a carboxymethyl ether (p—CME—EDDP). This was used to prepare protein conjugates either by direct condensation or via the linking group maleimido-ethylamine (p—MEA—CME—EDDP).

It was found that p—HO—EDDP derivatives are much more effective for generating specific anti-EDDP antibodies than prior art compounds. When coupled to the protein carrier KLH, both p—CME—EDDP and p—MEA—CME—EDDP elicited a number of specific antibody clones with minimal cross-reactivity to methadone or EMDP.

Figure 3:
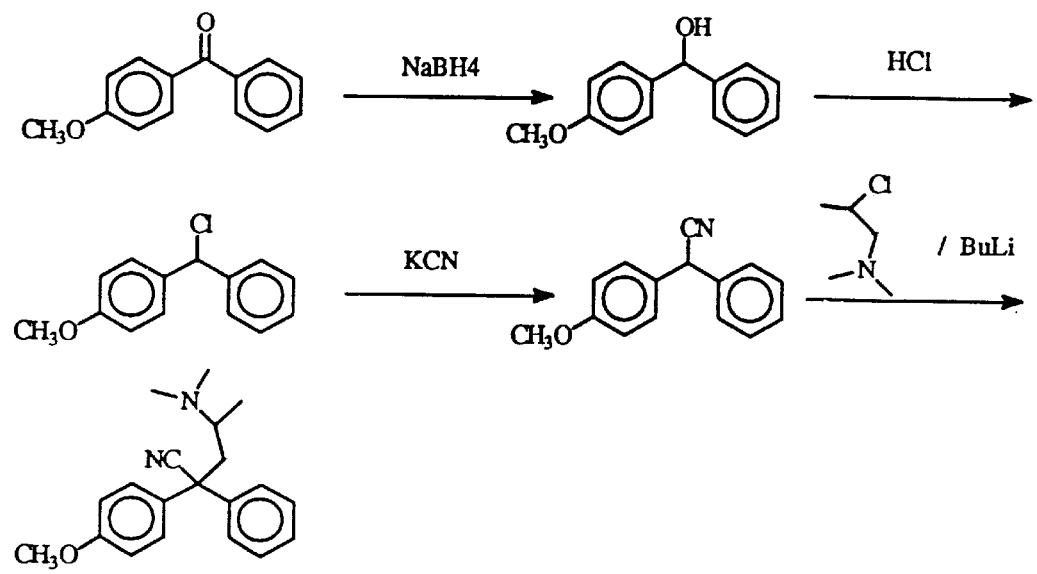
FIG. 3 is a chemical scheme showing the synthesis of 4-dimethylamino-2-(p-alkoxyphenyl)-2-phenylpentane-nitrile, where the alkoxyphenyl group is methoxyphenyl.
Figure 4:
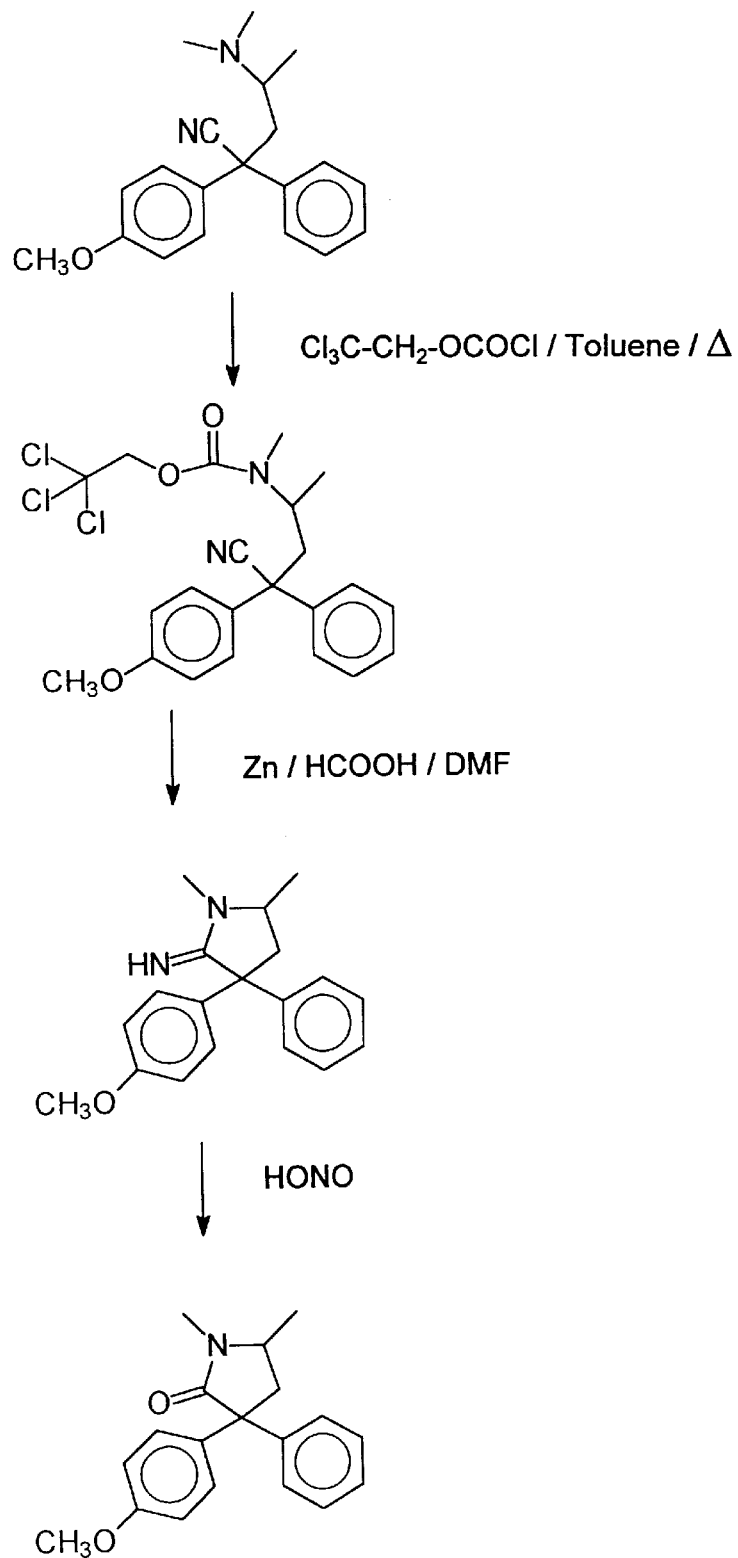
FIG. 4 is a chemical scheme showing the synthesis of a 1,5-dimethyl-3-(p-alkoxyphenyl)-3-phenyl-2-pyrrolidone, where the alkoxyphenyl group is methoxyphenyl.

The synthesis of the EDDP analogs of this invention is accomplished by first preparing the intermediate, para-hydroxy-EDDP (p—HO—EDDP). The synthesis is accomplished as follows: The starting material p-methoxybenzophenone is commercially available. This is elaborated to give the nitrile shown in FIG. 3. The nitrile is converted into the 1,5-dimethyl-3-p-methoxyphenyl-3-phenyl-2-pyrrolidone using the reaction scheme shown in FIG. 4.

Figure 5:
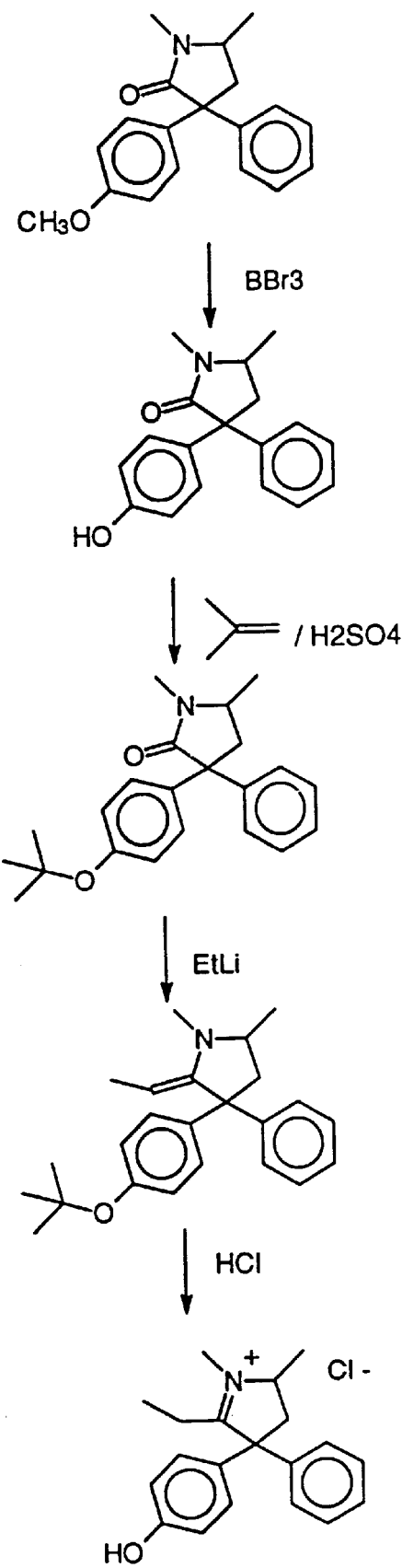
FIG. 5 is a chemical scheme showing the synthesis of the key intermediate 2-ethyl-1,5-dimethyl-3-p-hydroxyphenyl-3-phenylpyrroline (p—HO—EDDP) as a hydrochloride salt. Availability of p—HO—EDDP makes possible the preparation of a new family of EDDP chemical analogs and EDDP-protein conjugates as described in this disclosure.

In order to complete the synthesis, a more acid labile HO-protecting group than methoxy is used to prevent decomposition of the EDDP enamine during the final steps. A protecting group is chosen that is stable to the strongly basic conditions used when converting the pyrrolidone to the 2-ethylidene function by reacting with ethyllithium. Use of t-butyl ether as a protecting group fulfills these requirements. Thus, the p-methoxy-pyrrolidone is converted to the p-hydroxy-pyrrolidone by treatment with boron tribromide. The hydroxy group is converted into a t-butyl ether by acid catalyzed reaction with isobutylene to give the p—t-butoxy-pyrrolidone. This intermediate is reacted with ethyllithium to give the p—t-butoxy-EDDP. Finally, treatment with HCl in dioxane gives the p—HO—EDDP as a hydrochloride salt (FIG. 5).

Figure 6:
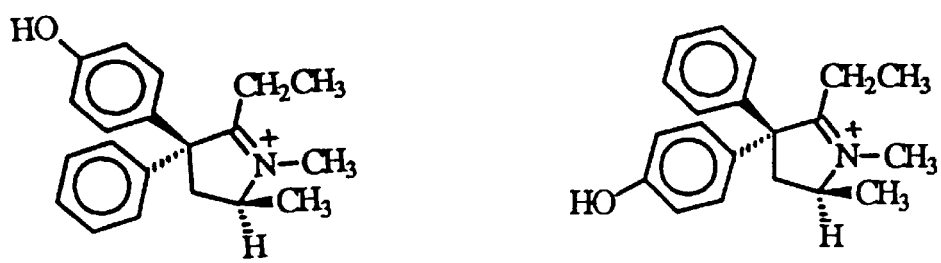
FIG. 6 is a drawing of two diastereomers of p—HO—EDDP.

The product of this procedure is a mixture of diastereomers as shown in FIG. 6,, which may be confirmed by HPLC or NMR.

The artisan of ordinary skill in the art will appreciate that the availability of preparative amounts of pure or synthetic p—HO—EDDP provides a gateway to a number of EDDP analogs, including those of the general form:

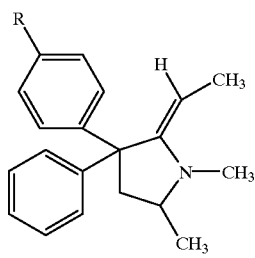

For example, the phenol group can be modified or conjugated according to any one of a number of standard chemical synthetic procedures, such as ether and ester formation, ring substitution and the like. Preferred embodiments are those in which R is a substituent having one or more N or C atoms, particularly an ether, ester, thioester, amine, or amide, and derivatives thereof that provide protein-reactive functional groups. Of particular interest are para-alkoxy analogs of EDDP.

Also of interest are EDDP analogs covalently conjugated to another substance or substituent, particularly through an alkoxy substituent in the para position, and optionally through a linker group. Of particular interest are proteins such as those used in immunogens or in enzyme-based immunoassays. However, this invention also embodies other usefull EDDP conjugates, including but not limited to EDDP conjugated to complex carbohydrates; EDDP conjugated to labeling reagents such as chromophores, chemiluminescent and bioluminescent compounds, and stable and unstable isotypes; and EDDP conjugated directly or indirectly to solid surfaces or particulates.

An EDDP analog or conjugate is said to be "purified" if it is (except from solvent) at least 50%, preferably at least about 90%, and even more preferably at least about 99% pure when analysed by a suitable technique such as GC/MS. A "synthetic" compound is a compound assembled from component parts by a process that does not involve live organisms or cells.

Various forms of EDDP and its analogs are interconvertible in aqueous solution according to the following scheme:

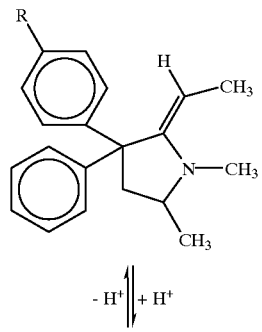

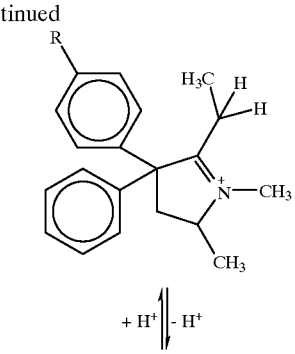

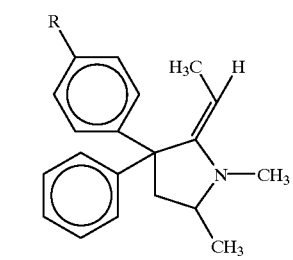

For the purposes of the present disclosure, these structures are considered to be equivalent. Where R is a substituent other than H, the compound comprises at least two chiral centers. The embodiments of this invention include all stereoisomers, tautomers, salts, and protonated and deprotonated forms of the structures shown unless otherwise indicated.

Certain preferred EDDP derivatives can be prepared by reacting p—HO—EDDP with a compound of the structure X-$R^0$ or X=$(R^0)_2$, where X is a leaving group. Preferred leaving groups are the halides Cl, Br, and I. This leads to ethers in which R is of the form $R^0$—O—. In some embodiments, $R^0$—is of the form Y—$R^1$— wherein $R^1$ is a hydrocarbyl diradical. Preferably, $R^1$ is a branched or unbranched hydrocarbyl diradical of 1–10 carbon atoms, or an alicyclic or aromatic hydrocarbyl diradical of 3-10 carbon atoms, or a combination thereof. Linear or branched alkyl diradicals are preferred, especially of the structure —$(CH_2)_m$— where m is 1 to 10, and particularly —$(CH_2)$—.

The substituent Y can have any structure of interest. Non-limiting examples include those wherein Y is H, —COOH, an ester of the form —$COOR^2$, an amide of the form —$CONHR^A$ or —$CONR^A R^B$, a thioether or thioester, any one of which may be further derivatized with other functional groups or conjugated to other substitutents, particularly protein, optionally through a linker group.

Where Y is —$COOR^2$, $R^2$ is typically a hydrocarbyl radical of 1–20 carbon atoms, preferably a branched or unbranched hydrocarbyl radical of 1–20 carbon atoms, or an alicyclic or aromatic hydrocarbyl radical of 3–20 carbon atoms, or a combination thereof. Linear or branched alkyi diradicals are preferred. t-butyl and other carboxylic acid protecting groups are especially preferred.

Figure 7:
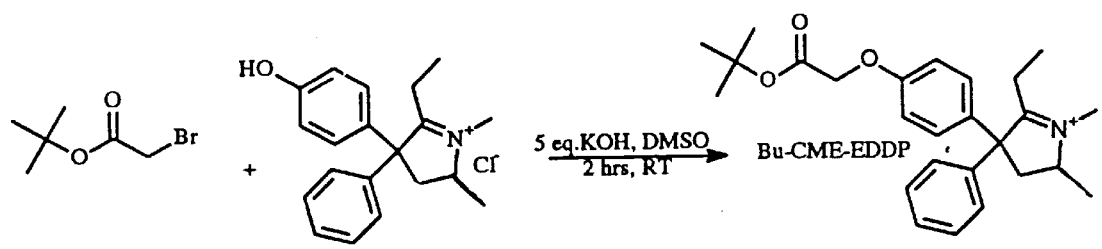
FIG. 7 is a chemical scheme showing the synthesis of the t-butyl-carboxymethyl ether of EDDP (p—t—Bu—CME—EDDP).
Figure 8:
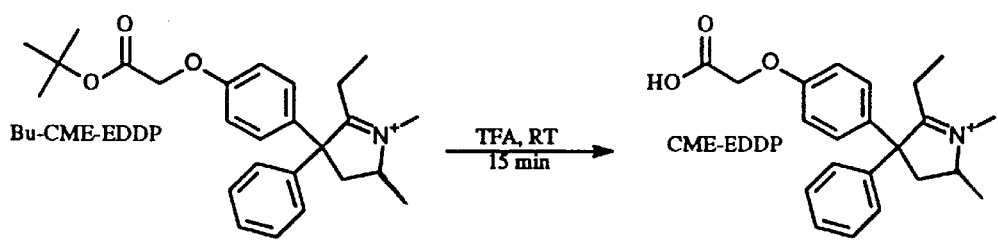
FIG. 8 is a chemical scheme showing the deprotection of p—t—Bu—CME—EDDP to yield the carboxymethyl ether of p—HO—EDDP (p—CME—EDDP). p—CME—EDDP and other carboxylated analogs of EDDP can be condensed with free amino groups on proteins to form EDDP-protein conjugates linked through an amide bond.

In one example, treatment of p—HO—EDDP with p—t-butyl bromoacetate and KOH in DMSO gives the alkylated ether, p-(t-butyl-carboxymethoxy)—EDDP (p—t—Bu—CME—EDDP), shown in FIG. 7. Quantitative deprotection of p-(t-butyl-carboxymethoxy)—EDDP is achieved by stirring in trifluoroacetic acid for about 15 min followed by lyophilization (FIG. 8). The structure of the resulting p-carboxymethoxy EDDP (p—CME—EDDP) may be confirmed by $^1$H—NMR and mass spectroscopy.

A deprotected carboxyl group conjugated to the p-alkoxy position of EDDP in this fashion is one example of a protein reactive group that can be used to attach a protein of interest. The carboxylic acid derivatives can be condensed directly with amine groups on a protein, for example, in the presence of a carbodiimide to yield an amide bond conjugate. Alternatively, the carboxylic acid is first converted to an active ester and then condensed in a subsequent reaction with free amino groups on the protein to yield an amide bond conjugate. In another procedure, an N-hydroxysuccinimide ester is first formed by reaction of the carboxylic acid with N,N-disuccinimidyl-carbonate (DSC). The active ester is then reacted with the protein to yield an arnide bond conjugate. In yet another procedure, the protein is conjugated to the p-carboxyalkoxy-EDDP using 1-ethyl-3-(3-dimethyl aminopropyl)carbodiimide (EDC) and N-hydroxysuccinimide (NHS) in DMF.

In other preferred embodiments of this invention, the protein is linked to an EDDP analog, not through an amide bond, but via a thioether bond. A maleimide adduct is first formed using an aminoalkyl-maleimide derivative. General synthesis of aminoalkyl-maleimide derivatives is described by Huber et al. in PCT Application No. PCT/EP90/00957. The maleimide adducts are then reacted with thiol groups on the protein to give a thioether-linked conjugate. Maleimide-sulfiydryl chemistry (Brinkley, Bioconjugate Chemistry 3:2–13, 1992) is generally more easy to control than amide bond condensation, allowing more exacting stochiometry of the conjugates which may be important for its intended function.

Starting with a carboxylic acid analog of EDDP, condensation with a maleimidohydrocarbylamine (preferably maleimidoethylamine) after preactivation of the carboxylic acid with N-hydroxysuccinimide and a carbodiimide, preferably 1-ethyl-3-(3'-dimethylaminopropyl)-carbodiimide (EDC), yields a maleimide adduct in which Y in the formula recited earlier has the general structure:

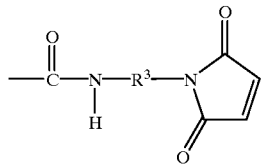

$R^3$ is preferably a hydrocarbyl diradical having 1–20 carbon atoms; either a branched or unbranched hydrocarbyl diradical of 1–20 carbon atoms, or an alicyclic or aromatic hydrocarbyl diradical of 3–20 carbon atoms, or a combination thereof Linear or branched alkyl diradicals are preferred, especially of the structure —(CH$_2$)$_n$— where n is 1 to 10, and particularly —CH$_2$CH$_2$— (in the case of maleimidoethylamine) or —(CH$_2$)$_5$— (in the case of maleimidopentylamine).

Figure 9:
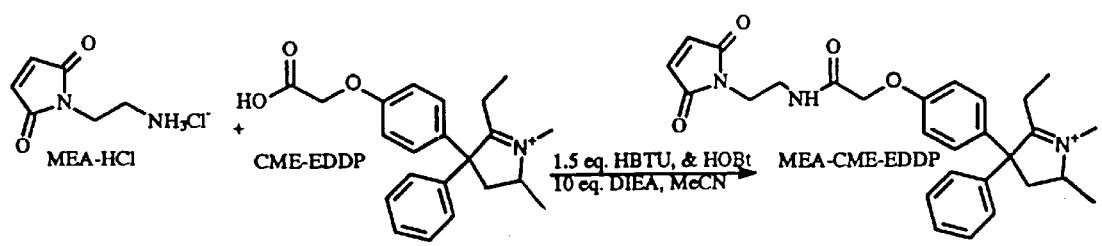
FIG. 9 is a chemical scheme showing the coupling of p—CME—EDDP with maleimidoethylamine (MEA) to yield the maleimide adduct p—MEA—CME—EDDP. This and other maleimide adducts of EDDP can be linked to proteins via thiol groups present as free cysteine side-chains or by thiolation of the protein with a reagent such as 2-iminothiolane (IT).

One illustration is shown in FIG. 9. p—CME—EDDP is coupled with maleimidoethylamine (MEA) using O-benzotriazol-1-yl-N,N,N',N'-tetramethyluronium hexafluorophosphate (HBTU) and 1-hydroxybenzotriazole hydrate (HOBt) in acetonitrile to yield p-(maleimidoethylamino-carbonylmethoxy) EDDP (p—MEA—CME—EDDP), which can be confirmed by $^1$H—NMR.

A protein conjugate can then be prepared by combining an excess of the maleimide adduct with a protein having free thiol groups. Free sulfhydryls may be provided in the form of free cysteine residues or by reducing protein disulfide bonds by a reagent such as dithiothreitol. Alternatively, thiol groups can be added to a protein having free primary amino groups by reacting with 2-iminothiolane (IT) in aqueous buffer, followed by removal of unreacted IT. A detailed protocol for the thiolation of the protein KLH is provided in U.S. Pat. No. 5,439,798.

The linkers of this invention are diradicals bonded in one position with a protein and in another position with EDDP analogs. Linkers are typically organic diradicals comprising 1–30 carbons and optionally O, N, and S, and may be aliphatic, alicyclic, aromatic, or any combination thereof. Certain preferred linkers are one or more alkyl diradicals bonded to each other, and to the peptide, and to the p—HO—EDDP or p-carboxyalkoxy-EDDP through any combination of ether, ester and amide linkages. Other preferred linkers are maleimidoalkylamine linkers of the general form:

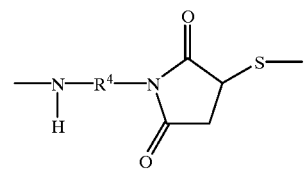

wherein $R^4$ has similar features to those described earlier for $R^3$.

The composition of the substituents $R^1$, $R^3$, and $R^4$ are generally chosen according to the desired features of the EDDP conjugate that is the object of the preparation. For example, where EDDP is coupled to a solid support or intact labeling agent, it may be desirable to use longer substituents in order to improve accessibility of the EDDP core. Coupling to enzyme donor polypeptides in a cloned enzyme donor immunoassay typically involve maleimidoethylamine adducts wherein $R^1$ is methylene, so that antibody binding will inhibit association with the enzyme acceptor. When preparing an immunogen, the substituents R1, R3, and R4 are generally as short as possible so as not to alter solubility characteristics and mininize the number of antibodies generated against the linker rather than EDDP. "Poly(amino acids)", "proteins", "peptides", and "polypeptides" are terms used interchangeably herein to describe polymers of amino acids of any sequence, typically at least 5 amino acids in length, linked by peptide bonds. Of particular interest are proteins that can be used as immunogenic carriers, and proteins that provide a detectable signal for assay purposes, particularly enzymes and enzyme donor polypeptides.

For the purposes of obtaining specific antibodies against EDDP, an EDDP-protein conjugate of this invention will comprise a plurality of EDDP analogs covalently bonded to an immunogenic protein carrier selected for its ability to provide a general immunostimulatory effect. Various protein carriers may be employed, including serum albumin, serum globulins, ocular lens proteins, lipoproteins, ovalbumin, thyroxine binding globulin, and synthetic polypeptides. Keyhole limpet hemocyanin (KLH) is especially preferred. KLH immunogens can be prepared by direct condensation with carboxyalkoxy-EDDP (e.g., KLH—p—CME—EDDP). Alternatively, KLH can be thiolated to provide thiol groups, for example, with IT, and then coupled with maleimidoalkylamine (e.g., KLH—IT—p—MEA—CME—EDDP).

The term "antibody" as used in this disclosure refers to both polyclonal and monoclonal antibody. The ambit of the term deliberately encompasses not only intact immunoglobulin molecules, but also such fragments and derivatives of immunoglobulin molecules as may be prepared by techniques known in the art, and retaining the antibody activity of an intact immunoglobulin. In this context, "antibody activity" refers to the ability of an antibody to bind a specific antigen in preference to other potential antigens via the antigen combining site located within a variable region of an immunoglobulin. Fragments and other derivatives of immunoglobulins can be prepared by methods of standard protein chemistry, such as subjecting the antibody to cleavage with a proteolytic enzyme like pepsin, papain, or trypsin; and reducing disulfide bonds with such reagents as dithiothreitol. Genetically engineered variants of intact immunoglobulin can be produced by obtaining a polynucleotide encoding the antibody, and applying the general methods of molecular biology to splice encoding sequences or introduce mutations and translate the variant. Antibodies that are engineered variants of particular interest include chimeric and humanized antibodies, Fab-like fragments, single-chain variable region fragments (scFv), and diabodies.

For general techniques used in raising, purifying and modifying antibodies, and the design and execution of immunoassays, the reader is referred to *Handbook of Experimental Immunology* (D. M. Weir & C. C. Blackwell, eds.); *Current Protocols in Immunology* (J. E. Coligan et al., eds., 1991); David Wild, ed., *The Immunoassay Handbook* (Stockton Press N.Y., 1994); and R. Masseyeff, W. H. Albert, and N. A. Staines, eds., *Methods of Immunological Analysis* (Weinheim: VCH Verlags gesellschaft mbH, 1993).

Polyclonal antibodies of this invention are raised by administration of the immunogenic EDDP-protein conjugate to a mammalian host, usually mixed with an adjuvant. The immunogen is conveniently prepared for injection by rehydrating lyophilized immunogen to form a solution or suspension. Preferred adjuvants are water-in-oil immersions, particularly Freund's complete adjuvant for the first administration, and Freund's incomplete adjuvant for booster doses. The preparation is typically administered in a variety of sites, and typically in two or more doses over a course of at least 4 weeks. Serum is harvested and tested for the presence of EDDP antibody using an EDDP-protein conjugate or other EDDP analog in a standard immunoassay or precipitation reaction.

Polyclonal antisera will typically contain antibodies not reactive with EDDP and anti-EDDP antibodies cross-reactive with other substances including methadone. Methods for purifying specific antibodies from a polyclonal antiserum are known in the art. A particularly effective method is affinity purification using a column of EDDP conjugated to a solid phase. One manner of preparing an EDDP column is to conjugate EDDP to a protein other than the protein used in the immunogen, and then attach the conjugate to a commercially available activated resin, such as CNBr-activated SEPHAROSE™. The anti-EDDP is passed over the EDDP column, the column is washed, and the antibody is eluted with a mild denaturing buffer such as 0.1 M glycine, 0.2 M NaCl, pH 2.5. If the anti-EDDP is passed over the column in a buffer containing free methadone, then the bound and eluted fraction will be enriched for antibodies that are EDDP specific and don't cross-react with methadone.

Monoclonal antibodies of this invention can be prepared by a number of different techniques known in the art. For hybridoma technology, the reader is referred generally to Harrow & Lane (1988), U.S. Pat. Nos. 4,491,632, 4,472, 500, and 4,444,887, and *Methods in Enzymology,* 73B:3 (1981). The most common way to produce monoclonal antibodies is to immortalize and clone a splenocyte or other antibody-producing cell recovered from an animal that has been immunized against EDDP as described earlier. The clone is immortalized by a procedure such as fusion with a non-producing myeloma, by transfecting with Epstein Barr Virus, or transforming with oncogenic DNA. The treated cells are cloned and cultured, and clones are selected that produce antibody of the desired specificity. Specificity testing is performed on culture supernatants by a number of techniques, such as using the immunizing antigen as the detecting reagent in an immunoassay. A supply of monoclonal antibody from the selected clone can then be purified from a large volume of culture supernatant, or from the ascites fluid of suitably prepared host animals injected with the clone. The antibody may be tested for activity as raw supernatant or ascites, and is optionally purified using standard biochemical preparation techniques such as ammonium sulfate precipitation, ion exchange chromatography, and gel filtration chromatography.

Alternative methods for obtaining monoclonal antibodies involve contacting an immunocompetent cell or viral particle with an EDDP-protein complex of this invention in vitro. In this context, "immunocompetent" means that the cell or particle is capable of expressing an antibody specific for the antigen without further genetic rearrangement, and can be selected from a cell mixture by presentation of the antigen. Immunocompetent eukaryotic cells can be harvested from an immunized mammalian donor, or they can be harvested from an unimmunized donor and prestimulated in vitro by culturing in the presence of immunogen and immunostimulatory growth factors. Cells of the desired specificity can be selected by contacting with the immunogen under culture conditions that result in proliferation of specific clones but not non-specific clones. Immunocompetent phage may be constructed to express immunoglobulin variable region segments on their surface. See Marks et al., New Engl. J. Med. 335:730, 1996; WO patent applications 94/13804, 92/01047, 90/02809; and McGuinness et al., Nature Biotechnol. 14:1149, 1996. Phage of the desired specificity may be selected, for example, by adherence to an EDDP-protein complex attached to a solid phase, and then amplified in *E. coli.*

Antibodies obtained using any of the aforementioned techniques are screened or purified not only for their ability to react with EDDP, but for a low cross-reactivity with potential interfering substances. "Cross reactivity" is determined in a quantitative immunoassay by establishing a standard curve using known dilutions of the target analyte, EDDP. The standard curve is then used to calculate the apparent concentration of the interfering substance present in various known amounts in samples assayed under similar condition. The cross reactivity is the apparent concentration divided by the actual concentration multiplied by 100. The preferred immunoassay for determining cross-reactivity is a CEDIA® type assay using an ED28-p—MEA—CME—EDDP donor polypeptide, described in detail in Example 4.

Acceptable levels of cross-reactivity of an anti-EDDP antibody for methadone are less than 5%, preferably less than 2%, more preferably less than about 1%, more preferably less than about 0.5%, even more preferably less than about 0.1%, and still more preferably less than about 0.02%. The antibody is also preferably less than 10%, more preferably less than 2%, more preferably less than 0.5% cross-reactive with EMDP. For purposes of monitoring methadone treatment, cross-reactivity with EMDP is generally less a concern than methadone. Since EMDP (like EDDP) is a naturally occurring methadone metabolite, its presence in a biological sample indicates compliance with treatment rather than sample tampering. It is generally worth screening antibodies for cross reactivity with other pharmaceutical compounds that subjects may be taking collaterally, particularly those eliminated in urine and having a polycyclic structure with some resemblance to EDDP. Relevant compounds include phenytoin and phenobarbital. Other compounds that were tested during the development of this invention are listed in Example 4. Levels of cross-reactivity for interfering compounds of this nature are preferably less than 0.1%, more preferably less than 0.01%.

Selection of a particular antibody for a specific use involves considerations more than just its cross-reactivity with potential interfering substances. Also relevant are such features as the reaction rates and affinity of the antibody which affect sensitivity and capacity of the reaction system, and the titer of antibody formed by a biological source. Ultimate selection may require a compromise between these various features.

Embodied in this invention are assay methods for the presence of EDDP and EDDP analogs in a sample of interest, including but not limited to subjects suspected of being administered methadone and related compounds, particularly humans. Suitable samples include biological samples (particularly urine and serum) taken from subjects, optionally diluted or modified to facilitate the assay, experimental samples generated by any chemical or biological method, and standards containing known concentrations of EDDP or other substances used for assay calibration.

In most instances, the assays will involve using an antibody raised against an EDDP-protein conjugate of this invention or having the characteristics of such an antibody, particularly a low cross-reactivity with methadone itself.

The procedure entails combining the sample with the antibody under conditions that permit the formation of a stable complex between the substance to be tested (described herein as the "analyte", and typically EDDP), and the antibody. This is followed by detecting any EDDP-antibody complex that is formed. A "stable complex" is a complex between antibody and analyte (typically non-covalently associated) that persists at least as long as it takes the presence of the complex to be measured by the intended method.

The antibodies and EDDP conjugates of this invention may be implemented in any assay method known in the art.

Assays of this invention include both qualitative and quantitative assays. Typical quantitative methods involve mixing the analyte with a predetermined non-limiting amount of the reagent antibody, and correlating the amount of complex formed with the amount of analyte in the original sample using a relationship determined using standard samples containing known amounts of analyte in the range expected for the sample to be tested. In a qualitative assay, sufficient complex above or below a threshold level established by samples known to contain or be free of analyte establish the assay result. Unless otherwise required, "measuring" can refer alternately to qualitative and quantitative determination.

Assays of this invention include both separation-based and homogeneous assays. In separation based assays, the detecting of the complex involves a process wherein the complex formed is physically separated from either unreacted analyte, unreacted antibody, or both. See, e.g., U.S. Pat. No. 3,646,346. The complex may be first formed in the fluid phase, and then subsequently captured by a solid phase reagent or separated on the basis of an altered physical or chemical property, such as by gel filtration or precipitation. Alternatively, one of the reagents may be attached to a solid phase before contacting with other reagents, and then the complex may be recovered by washing the solid phase free of unreacted reagents. Separation-based assays typically involve use of a labeled analog or antibody to facilitate detection or quantitation of the complex. Suitable labels are radioisotopes such as $^{125}$I, enzymes such as peroxidase and β-galactosidase, and fluorescent labels such as fluorescein isothiocyanate. The separation step involves removing labeled reagent present in complex form from unreacted labeled reagent. The amount of label in the complex can be measured directly or inferred from the amount left unreacted.

In homogeneous assays, the complex is typically not separated from unreacted reaction components, but instead the presence of the complex is detected by a property which at least one of the reactants acquires or loses as a result of being incorporated into the complex. Homogeneous assays known in the art include systems involving fluorochrome and fluorochrome quenching pairs on different reagents (U.S. Pat. Nos. 3,996,345, 4,161,515, 4,256,834, and 4,261,968); enzyme and enzyme inhibitor pairs on different reagents (U.S. Pat. Nos. 4,208,479 and 4,233,401); and chromophore and chromophore modifier pairs on different reagents (U.S. Pat. No. 4,208,479). A preferred homogeneous assay system is the cloned enzyme donor immunoassay, described in more detail below.

Assays of this invention include both sandwich and competition assays. Sandwich assays typically involve forming a complex in which the analyte to be measured is sandwiched between one reagent, such as a first antibody used ultimately for separation of the complex, and another reagent, such as a second antibody used as a marker for the separated complex. Competition assays involve a system in which the analyte to be measured competes with an analog of the analyte for binding to another reagent, such as an antibody. In the context of immunoassay, an "EDDP analog" refers to a compound that is able to compete with EDDP for binding to the antibody being used in the assay. EDDP analogs of this invention useful in immunoassay techniques include but are not limited to EDDP-radioisotope conjugates, EDDP-enzyme conjugates, and other EDDP-protein complexes. CEDIA® is an example of a competition assay. The invention also embodies assays that are neither sandwich nor competition assays, as in certain assays involving immunoprecipitation.

Immunoassays specific for EDDP using anti-EDDP antibodies of this invention are rendered specific by virtue of the specificity of the antibody. For assays further employing EDDP-protein conjugates (such as when EDDP is labeled with an enzyme polypeptide), the EDDP can be attached to the protein conjugate by any suitable method. In certain preferred embodiments, the chemistry described herein for formation of para-alkoxy analogs of EDDP is also used to prepare the EDDP-protein conjugate used as an assay reagent. In this way, the EDDP core is presented to the antibody in about the same orientation as during the immunization event when the antibody was generated.

Assay methods of this invention are exemplified in the cloned enzyme donor immunoassay, described in U.S. Pat. No. 4,708,929. Related reagents and methods are taught in U.S. Pat. Nos. 5,254,577; 5,444,161; 5,464,747; and 5,514,560. Cloned enzyme donor immunoassays for procainamide and N-acetylprocainamide (NAPA) are described in U.S. Pat. Nos. 5,439,798 and 5,525,474. For the purposes of patent prosecution in the U.S., the aforelisted patents are hereby incorporated herein in their entirety. Cloned enzyme donor immunoassays are available commercially under the registered trademark CEDIA®. The reader is referred to CEDIA® product inserts and technical manuals for further information.

Typically, a cloned enzyme donor immunoassay of this invention involves combining the sample with: an EDDP-specific antibody; an enzyme donor polypeptide conjugate; an enzyme acceptor polypeptide (wherein the enzyme acceptor polypeptide is capable of forming with said enzyme donor polypeptide conjugate an active enzyme complex in the absence of an antibody to EDDP), and a substrate capable of being transformed by the active enzyme complex into a product. The amount of product is then measured, usually as a function of time.

The EDDP-specific antibody is preferably an antibody raised against an EDDP-protein conjugate of this invention, or having the characteristics of such an antibody, especially a low level of cross-reactivity with methadone. The antibody is also selected on the basis of three other criteria. One, referred to as "inhibition", relates to how well the antibody binds the enzyme-donor conjugate. Sufficient inhibition (preferably at least about 70%) is needed in order to provide an adequate signal. A second criterion is the titer of the antibody required to obtain the desired level of inhibition. Inhibition at lower antibody levels is preferred. A third criterion, referred to as "modulation", relates to how well the sample analyte is able to compete with the conjugate for enzyme binding. Modulation is calculated as the difference in enzyme rate between a sample having the analyte at a target concentration (moderately chosen within the intended working range; preferably 100 ng/mL in the case of EDDP) and a sample having no analyte, divided by the rate at the target concentration. Better modulation correlates with better assay sensitivity.

The enzyme-donor enzyme-acceptor pair is a pair of polypeptides which spontaneously assemble in reagent buffer to form an active enzyme complex. The active enzyme complex is capable of enzymatically transforming a substrate into a product that is differentially detectable. Typically, the product is a different color from the substrate and can be quantified in a spectrophotometer. The donor and acceptor pair are typically two functional subunits of a common enzyme. The subunits may be noncovalently associated in the native enzyme, or they may be defective versions of a common polypeptide that complement each other when together.

Preferred enzyme-donor and enzyme-acceptor polypeptides are based on the enzyme β-galactosidase polypeptide. A "β-galactosidase polypeptide" is a polypeptide identifiable on the basis of its amino acid sequence or enzymatic activity as being developed from an enzyme with β-galactosidase activity. The definition encompasses not only naturally occurring β-galactosidase, but also fragments, deletion mutants, fusion proteins, mutants, and other variants based thereupon obtained by such processes as enzymatic fragmentation and genetic engineering of relevant encoding sequences. Particular β-galactosidase polypeptides are described in the aforelisted U.S. patent applications pertaining to cloned enzyme donor immunoassays.

β-galactosidase enzyme acceptors are preferably produced by a deletion mutant of the β-galactosidase gene. EA22, one of the preferred acceptors, has a deletion of amino acid residues 13–40. Other enzyme acceptor fragments of β-galactosidase which contain the natural sequence which includes amino acid position 602 may also be used. Other examples include EA5, EA11, EA14, EA17, EA18, EA20, EA23 and EA24. The distal end of the deleted segment normally falls between amino acid positions 26 and 54 of the β-galactosidase sequence. In EA22, the distal end of the deletion segment is amino acid 40.

A particularly preferred β-galactosidase enzyme donor is ED28. This is a fragment of β-galactosidase consisting of amino acids 1–46, with cysteine residues at positions 1 and 46. ED28 is described in European Patent Application No. 90308937.3. The two cysteine residues can be used for exact and reproducible placement of maleimide adducts of EDDP as described earlier. Before conjugation with EDDP, reducing reagent that is generally used in the storage of ED28 is removed by a suitable desalting technique, such as on a Pharmacia NAP5™ column as described in U.S. Pat. No. 5,439,798. The EDDP is then conjugated with the maleimide adducts as described elsewhere in this disclosure. Adjustment of the linkage can be performed by monitoring enzyme inhibition by an EDDP-specific antibody. Typical linker groups used are maleimide adducts having the structure indicated earlier, wherein $R^4$ is —$(CH_2CH_2)$—.

Preferred substrates for use in immunoassays based on β-galactosidase include those described in U.S. Pat. Nos. 5,032,503; 5,254,677; 5,444,161 and 5,514;560. Amongst the preferred substrates is chlorophenol B—D-red galactopyranoside. Optimization of other features and conditions of the assays embodied by this invention is a matter of routine experimentation within the skill of the ordinary artisan.

Reagents and buffers used in the assays of this invention can be packaged separately or in combination into kit form to facilitate distribution. The reagents are provided in suitable containers, and typically provided in a package along with written instructions relating to assay procedures.

Further illustration of the development and use of antibodies and assays according to this invention are provided in the Example section below. The examples are provided as a further guide to a practitioner of ordinary skill in the art, and are not meant to be limiting in any way.

EXAMPLES

Example 1

Synthesis of racemic 1,5-dimethyl-3-(p-methoxyphenyl)-3-phenyl-2-pyrrolidone

General Procedures p-Methoxybenzophenone and 2-dimethyl-aminoisopropyl chloride hydrochloride were purchased from Aldrich Chemical Co. Melting points (m.p.) were determined on a Hoover capillary apparatus and are uncorrected. The IR spectrum was recorded on a Shimadsu IR-460 spectrophotometer. $^1$H—NMR spectra were obtained on a Bruker WM-250 NMR spectrometer. Analytical precoated TLC plates (5×10 cm) were purchased from Merck. The TLC plates were visualized using phosphomolybdic acid and then $Ce(SO_4)_2$ in sulfuric acid spray reagents.

p-methoxybenzhydryl alcohol

Solid $NaBH_4$ (2.55 g, 0.067 mol) was added portion-wise to a solution of p-methoxybenzophenone (25.14 g, 0.118 mol) in MeOH (150 mL) at room temperature over 10 min. After the exothermic reaction had subsided, the reaction mixture was stirred at room temperature for 2 h. TLC ($SiO_2$, $CHCl_3$) indicated incomplete reaction; therefore, additional $NaBH_4$ (2.55 g) was added and the reaction mixture was stirred at room temperature an additional 2 h. The MeOH was evaporated and the residue partitioned between water (100 mL) and $CH_2Cl_2$ (100 mL). The layers were separated, and the aqueous layer was extracted with $CH_2Cl_2$ (200 mL). The combined organic layers were dried ($Na_2SO_4$), filtered and evaporated to give the alcohol (25.24 g, 99%) as a white solid: m.p. 66–67° C. The structure was confirmed by $^1$H—NMR in $CDCl_3$.

p-methoxybenzhydryl chloride

A stirred suspension of p-methoxybenzhydryl alcohol (25.04 g, 0.117 mol) and $CaCl_2$ (38.22 g, 0.344 mol) in benzene (400 mL) was bubbled with hydrogen chloride gas for 45 min. Afterwards, the mixture was stirred an additional 1 h and then filtered. The filtrate was evaporated to give the chloride (27.10 g, 99%) as an off-white solid. The structure was confirmed by $^1$H—NMR in CDCl$_3$.

2-(p-methoxyphenyl)-2-phenylacetonitrile

To a solution of p-methoxybenzhydryl chloride (27.00 g, 0.116 mol) in dry CH$_3$CN (200 mL) was added dibenzo-18-crown-6 (2.12 g) followed by dry KCN (8.02 g, 0.123 mol), and the stirred mixture was refluxed for 66 h. After this time, the reaction mixture was cooled to room temperature and the solid was removed by filtration. The filtrate was evaporated under vacuum. The resulting solid was dissolved in CH$_2$Cl$_2$ (50 mL) and the solution flushed through a silica gel column (230–400 mesh, 60 g) using CH$_2$Cl$_2$. The eluent was evaporated and the residue was titurated with heptane to precipitate the product. The precipitate was collected and washed with heptane to give a solid. $^1$H—NMR analysis of this solid showed that it was a mixture of starting chloride and product. Therefore, the heptane filtrates were evaporated and the solids were recombined, giving a total of 25.03 g of material. This solid was reacted again as described above, except that the reflux period was extended 48 h. Afterwards, the reaction mixture was worked up as described above to give the title nitrile (18.56 g, 72%) as a yellowish white solid. The structure was confirmed by $^1$H—NMR in CDCl$_3$.

4-dimethylamino-2-p-methoxyphenyl)-2-phenylpentanenitrile

The THF used in this procedure was freshly distilled from benzophenone/Na metal, and the glassware was oven-dried at 120° C. for 4 h. To a 1000 mL three neck round-bottom flask flushed with nitrogen was added THE (30 mL). The flask was cooled in an ice bath, then 2.5M n-butyllithium in hexane (29.6 mL, 0.074 mol) was added by syringe followed by diisopropylamine (7.48 g, 0.074 mol) to give a yellow solution. To the cold stirred solution was added a solution of 2-(p-methoxyphenyl)-2-phenylacetonitrile (15.00 g, 0.0672 mol) in THF (300 mL) drop-wise over 15 min to give a dark yellow solution. Then a solution of 2-dimethylaminoisopropyl chloride (35.95 g, 0.294 mol) in THF (40 mL) was added and the reaction mixture was heated to gentle reflux under nitrogen. After refluxing for 18 h, the reaction was complete by TLC (SiO$_2$, CHCl$_3$). The reaction mixture was cooled to room temperature then evaporated under vacuum to an oily residue. The residue was partitioned between ether (300 mL) and water (300 mL). The layers were separated and the ether layer was washed with saturated NaCl (300 mL), then dried (Na$_2$SO$_4$). The ether was filtered, and the filtrate evaporated under vacuum to give a viscous yellow oil (22.55 g). The oil was chromatographed on silica gel (230–400 mesh, 1000 g) using 1% acetone/CHCl$_3$ (6000 mL), 2% acetone/CHCl$_3$ (4000 mL), 3% acetone/CHCl$_3$ (1000 mL), 5% acetone/CHCl$_3$ (8000 mL), 10% acetone/CHCl$_3$ (7000 mL) and acetone (3000 mL) to give the title nitrile (13.53 g, 65%) as a viscous yellow oil. The structure was confirmed by $^1$H—NMR in CDCl$_3$.

4-(N-2,2,2-trichlorocarboethoxy-N-methylamino)-2-(p-methoxyphenyl)-2-phenylpentanenitrile A stirred solution of 4-dimethylamino-2-(p-methoxyphenyl)-2-phenylpentanenitrile (13.43 g, 0.044 mol) in toluene (100 mL) was heated to reflux under nitrogen and a solution of 2,2,2-trichloroethylchlorofornate (10.70 g, 0.051 mol) in toluene (50 mL) was added drop-wise over 30 min. The reaction mixture was refluxed for 24 h. TLC [SiO$_2$, CHCl$_3$:MeOH:conc. NH$_4$OH (90/10/4 drops per 100 mL)] indicated incomplete reaction; therefore, additional 2,2,2-trichloroethylchloroformate (5.35 g) was added and the reaction mixture was refluxed another 24 h. After this time, the reaction mixture was cooled to room temperature and treated with 88% formic acid (6 mL) followed by triethylamine (14 mL), added slowly. Afterwards, water (200 mL) was added and the layers were separated. The aqueous layer was extracted with ether (200 mL). The organic layers were combined and washed with 10% HCl (2×250 mL) and saturated NaCl (200 mL). The organic layer was dried (Na$_2$SO$_4$) and evaporated under vacuum to obtain a viscous yellow oil (23.04 g). The oil was chromatographed on silica gel (230–400 mesh, 500 g) using CHCl$_3$ to give a title nitrile (18.60 g, 91%) as a viscous yellow oil. The structure was confirmed by $^1$H—NMR in CDCl$_3$.

2-imino-1, 5-dimethyl-3-(p-methoxyphenyl-3-phenyl-pyrrolidine hydrochloride

A solution of 4-(N-2,2,2-trichloro-carboethoxy-N-methylamino)-2-(p-methoxyphenyl)-2-phenyl-pentanenitrile (18.48 g, 0.039 mol) in dry DMF (150 mL) was cooled in an ice bath under nitrogen for 30 min. To the cold stirred solution was added 95% formic acid (4.3 g) followed by Zn dust (5.5 g) and the reaction mixture was stirred at room temperature for 48 h. Afterwards it was filtered, washing the solid with CH$_2$Cl$_2$ (100 mL). The filtrate was evaporated under vacuum using a vacuum pump to give an oil. The oil was dissolved in CHCl$_3$ (200 mL) and the solution was washed with 10% NH$_4$OH (2×100 mL). The combined aqueous layers were extracted with CHCl$_3$ (100 mL). The CHCl$_3$ layers were combined, dried, (Na$_2$SO$_4$) and evaporated under vacuum to obtain a viscous yellow oil (12.47 g). The oil was dissolved in ether (400 mL) and the solution was extracted with 10% HCl (2×100 mL). The aqueous layers were combined and extracted with ether (2×200 mL) and then with CHCl$_3$ (3×100 mL). The CHCl$_3$ extracts were combined, dried (Na$_2$SO$_4$) and evaporated to give the crude imine hydrochloride (11.36 g, 87%) as a tan foam. The structure was confirmed by $^1$H—NMR in CDCl$_3$.

1,5-dimethyl-3-(p-methoxyphenyl)-3-phenyl-2-pyrrolidone

A solution of crude 2-imino-1,5-dimethyl-3-(p-methoxyphenyl)-3-phenylpyrrolidine hydrochloride (11.26 g, 0.034 mol) in 10% HCl (500 mL) was heated to a steam bath. While heating on the steam bath, KNO$_2$ (100 g) was added portion-wise over 30 min. CAUTION! The reaction foams with each addition. Following the addition of KNO$_2$ the reaction mixture was heated on the steam bath for 30 min. Additional 10% HCl (100 mL) was added followed by another portion-wise addition of KNO$_2$ (50 g), after which the reaction mixture was heated for 30 min. Afterwards, the reaction mixture was cooled to room temperature and extracted with ether (3×200 mL). The combined ether layers were dried (MgSO$_4$) and evaporated under vacuum to obtain a viscous yellow oil (7.78 g). The oil was chromatographed on silica gel (230–400 mesh, 400 g) using CHCl$_3$ to give the title compound (5.99 g, 70%) as a viscous yellow oil. The structure was confirmed by $^1$H—NMR in CDCl$_3$, and characterized by IR in CHCl$_3$. The final yield after additional drying, characterization and transfer was 4.87 g.

Analysis

Calculated for C$_{19}$H$_{21}$NO$_2$•CHCl$_3$: C, 75.93; H, 7.04; N, 4.65. Found: C, 76.15; H, 7.19; N, 4.72.

Example 2

Synthesis of racemic 2-ethyl-1.5-dimethyl-3-p-hydroxyphenyl-3-phenylpyrroline hydrochloride (+/−)-1, 5-dimethyl-3-(-hydroxyphenyl)-3-phenyl-2-pyrrolidone (+/−)-1,5-dimethyl-3-(p-hydroxyphenyl)-3-phenyl-2-pyrrolidone (from Example 1), 1.5 g, was dissolved in 30 mL dichloromethane. The flask was flushed with argon and chilled in an acetone/dry ice bath to −60° C. 1 M boron tribromide in dichloromethane, 10 mL, was then added drop-wise over 18 min with stirring. The reaction was allowed to come to room temperature and stirred for 22 h. Methanol, 10 mL, was then added slowly to quench the reaction. The resultant solution was rotary evaporated to give an oil redissolved in 10 mL methanol and rotary evaporated a second time. The oil was diluted with 20 mL water to give a precipitate. 6 N hydrochloric acid, 6 mL, was added followed by 50 mL dichloromethane. Mixing gave a biphasic solution. The phases were separated and the upper aqueous phase was reextracted twice with 25 mL portions of dichloromethane. The combined dichloromethane extracts were washed with saturated sodium chloride solution, dried over sodium sulfate, and evaporated to give a foam residue.

The product was crystallized from diethyl ether to give 1.0 g. m.p. 164–170° C. (uncorrected); TLC: Chlorofoinl-methanol (9:1) silica 60 F254—single UV absorbing and iodine staining spot at Rf0.15. $^1$H—NMR(CDCl$_3$): 1.26 ppm (d,d), 5 CH$_3$; 2.2 and 2.9 ppm (ms), 4 CHs; 2.89 ppm(s), 1 N—CH$_3$; 3.5 ppm (m), 5 CH; 6.1 ppm (d), p—HO; 6.6 and 7.1 ppm (dds), p—HO-phenyl; 7.3 ppm (m), phenyl.

(+/−)-1,5-dimethyl-3-(p-tert-butoxyphenyl)-3-phenyl-2-pyrrolidone (+/−)-1,5-dimethyl-3-(p-tert-butoxyphenyl)-3-phenyl-2-pyrrolidone, 516 mg, was suspended in 12 mL of dichloromethane. The flask was purged with argon. Concentrated sulfuiric acid, 20 μl, was then added and isobutylene was bubbled in slowly through a sparging tube. After one h an additional 9 mL of dichloromethane and 10 μl of sulfuric acid were added, and the flask was stoppered and allowed to stand at room temperature for 18 h. The reaction mixture was then diluted with 10 mL water and mixed to obtain a biphasic solution. The phases were separated and the lower dichloromethane phase was washed with saturated sodium chloride solution, dried over sodium sulfate and rotary evaporated to give an oil. The crude product contained some starting material and side product.

Purification by silica gel flash chromatography in acetone/chloroform (9:1) gave 454 mg of an oily product. TLC: chloroform/acetone 9:1; silica 60 F254, single UV absorbing and iodine staining spot Rf0.5; 1H—NMR (CDCl$_3$: 1.27 ppm (m) 5-CH3 overlapped with 1.32 ppm (s) t—Bu CH3s; 2.2 and 3.0 ppm (ms), 4 CHs: 2.9 ppm (s) 1 N-CH3; 3.5 ppm (m), 5 CH; 6.9 ppm (d) p—tBuO-phenyl; 7.2–7.4 ppm (ms), p—tBuO-phenyl and phenyl.

(+/−)-2-ethylidene-1,5-dimethyl-3-(p-tert-butoxyphenyl)-3-phenylpyrrolidine

Ethyl lithium was prepared fresh by weighing out 84 mg of lithium ribbon under argon and transferring to a Schlenk flask equipped with a dropping finnel plus magnetic stir bar and purged with argon. Anhydrous diethyl ether, 10 mL, was added to the flask. The flask was then cooled to −40° C. in an acetone/dry ice bath. In the meantime, a solution of 710 mg of bromoethane in 8 mL ether was prepared and added to the dropping funnel. The bromoethane solution was added to the vigorously stirred lithium suspension over 5 min at −40° C. to −5° C. to give a turbid, nearly colorless solution of ethyl lithium.

(+/−)-1,5-dimethyl-3-(p-tert-butoxyphenyl)-3-phenyl-2-pyrrolidone, 717 mg, was then dissolved in 8 mL toluene and transferred to the dropping funnel. The solution was added drop-wise to the stirred ethyl lithium at −5° C. over 5 min. The reaction was then allowed to warm up to room temp over 1 h. After 80 min at room temp, the reaction was quenched by drop-wise addition of 10 mL ice water. The biphasic mixture was separated and the upper organic phase was washed with water followed by saline solution. The organic phase was dried over magnesium sulfate, filtered and rotary evaporated to give 656 mg of crude product as a mixture of cis and trans isomers.

TLC n-butanol/acetic acid/ water 4:1:1; silica 60 F254; major UV absorbing, iodine staining spot at Rf0.42; minor spot at Rf0.50. $^1$H—NMR (CDCl$_3$): 0.92 ppm (m), cis ethylidene CH$_3$; 1.09–1.15 ppm (ds) cis/trans 5-CH$_3$; 1.31 ppm (s) & 1.37 ppm (s), cis/trans t—BuO CH$_3$s; 1.7 ppm (m), trans ethylidene CH$_3$; 2.35 ppm (s) & 2.63 ppm (s), cis/trans 1-N—CH$_3$s; 3.6 ppm (m), trans ethylidene CH; 4.3 ppm (m), cis ethylidene CH; 6.8–7.5 ppm (ms), ArH.

(+/−)-2-ethyl-1,5-dimethyl-3-(p-hydroxyphenyl-3-phenylpyrroline hydrochloride (p—HO—EDDP.HCl)

(+/−)-2-ethylidene-2.5-dimethyl-3-(p-tert-butoxyphenyl)-3-phenylpyrrolidine, 648 mg, was dissolved in 4 mL dioxane, purged with argon, then diluted with 4 mL of 4 N hydrogen chloride/dioxane reagent. The reaction was stirred at room temp. for 3 h. The resultant orange red solution with some reddish solids was filtered through a sintered glass funnel and the filtrate was diluted with 50 mL diethyl ether to obtain an oily red precipitate. The other was decanted and the oil was washed with fresh ether by sonication. The ether was decanted and the oil was dissolved in 100 mL chloroform.

The solution was rotary evaporated in a taxed flask to give 311 mg of product as a pale red-orange foam. $^1$H—NMR (CD$_3$CN): Endocyclic double bond; two diastereomers; 0.6 ppm (overlapping ts="d of d"), 2-ethyl CH$_3$ 1.55 ppm (d of d), 5-CH$_3$; 2.3–2.7 ppm (d of q), 4 CH; 2.75 ppm (q), 2-ethyl CH$_2$; 3.0–3.3 (d of q), 4 CH; 3.5 ppm (2 s="d"), 1-N-CH$_3$s; 4.5 ppm (2 overlapping qs), 5 CH; 7.0–7.6 ppm, Ar—H Mass spec [M+H]=294.3=theory; HPLC : C4RP; 5 min at 16% CH$_3$CN/20 mM triethylamine acetate pH 6 (TEA—Ac) followed by 16–46% CH$_3$CH/20 mM TEA—Ac (0.75%/min); flow 1 mL/min; monitored at 234 & 252 nm: two peaks with k'=5.58 (major) and 6.19 (minor).

Example 3

Preparation of p—HO—EDDP adducts, immunogens, and conjugates

Alkylation of p—HO—EDDP

Freshly ground KOH (13.2 mg 200 μmoles) was stirred under 200 μl DMSO for 5 min. p—HO—EDDP.HCl (13.2 mg. 40 μmoles), prepared as in Example 2, was added, followed by t-butyl bromoacetate (25.4 mg. 120 μmoles). After stirring for 110 min 3 mL of 20 mM, trifluoroacetic acid (ITA) in water was added followed by 4 μl additional neat TFA. The mixture was purified in two injections by HPLC (1×25 cm C4 column; Buffer A=20 mM TFA in water, Buffer B=20 mM TFA in CH$_3$NC; 0 min, 100% A; 0.1–10 min, 25% to 35% B; 10.1–20 min, 45% to 50% B; flow rate=4 mL/min; 280 nm) on a 10 mL loop. Lyophilization yielded p—t-butyl-carboxymethoxy-EDDP (p—t—Bu—CME—EDDP) (14.5 mg 69%) as pale red droplets.

Deprotection of p—t—Bu—CME—EDDP

TFA (1 mL) was added to p—t—Bu—CME—EDDP (19.4 mg 37.1 μmole) with stirring. After stirring for 15 min at room temperature (RT) the solution was frozen in liquid nitrogen and lyophilized to yield p—CME—EDDP (18.5 mg, 107%, retains some TFA) as pale red droplets. $^1$H—NMR (200 MHz, CD$_3$CN) ppm 6.95–7.45 (9 H, m, ArH), 4.70 (2 H, s, OCH$_2$CON), 3.50 (3 H, s, CH$_3$N) 3.1 & 3.3 (1 H @, 4-CH$_2$, dd, J$_a$=X Hz, J$_b$=X Hz), 0.59 (3 H, dt, J=2.4, 7.6 Hz, CH$_3$CH$_2$) MS (M+,352.2).

Coupling of p—CME—EDDP with Maleimidoethylamine (MEA)

MEA—HCl (5.30 mg, 20 μmoles), O-benzotriazol-1-yl-N,N,N',N'-tetramethyluronium hexafluorosphosphate (HBTU) (7.59 mg, 15 μmoles), 1-hydroxybenzotriazole hydrate (HOBt) (2.70 mg, 15 μmoles) and disopropylethylamine (DIEA) (12.9 mg, 100 μmoles) were added with stirring to p—CME—EDDP (4.66 mg, 10 μmoles) in 1 mL $CH_3CN$. After an hour, 8 mL of 0.1% aqueous TFA were added to the mixture. The resulting solution was purified in a single injection on a 10 mL loop by HPLC (1×25 cm C4 column; 0 min, 100% A; 0.1–20 min, 10 to 50% B; flow rate=4 mL/min; 260 nm). Lyophilization gave maleimidoethylamino-carbonylmethyl ether-EDDP (p—MEA—CME—EDDP) (4 mg 68%) as a hygroscopic red foam $^1H$ NMR (200 MHz, $CD_3CN$) ppm (minor isomer): 0.59 (3 H, t, J=7.6 Hz, 2-$CCH_2CH_3$). 1.43 (3 H, d, J=6.8 Hz, 5-$CH_2CH_3$), 2.46 (1 H, dd, J=6.6, 7.4 Hz, 4-$CH_aCH_b$), 2.72 (2 H, m, 2-$CCH_2$), 3.15 (1 H, dd, J=6.6 Hz, 7.3 Hz, 4-$CH_aCH_b$), 3.41 (2 H, t, J=5.9 Hz, $CH_2NCO$ 3.51 (3 H, s, $CH_3N$); 3.59 (2 H, t, J=5.6 Hz, $CH_2NCO$); 4.42 (2 H, s, $OCH_2CON$); 6.72 (2 H, s, maleimide); 6.97–7.44 (9 H, m, ArH); ppm (major isomer): 0.60 (3 H, t, J=7.6 Hz, 2-$CCH_2CH_3$). 1.47 (3 H, d, J=6.6 Hz, 5-$CH_2CH_3$), 2.56 (1 H, dd, J=6.2, 7.7 Hz, 4-$CH_aCH_b$), 2.72 (2 H, m, 2-$CCH_2$), 3.24 (1 H, dd, J=6.4 Hz, 7.7 Hz, 4-$CH_aCH_b$), 3.41 (2 H, t, J=5.9 Hz, $CH_2NCO$), 3.51 (3 H, s, $CH_3N$), 3.59 (2 H, t, J=5.6 Hz, $CH_2NCO$); 4.42 (2 H, s, $OCH_2CON$); 6.76 (2 H, s, maleimide); 6.97–7.44 (9 H, m, ArH).

Preparation of KLH—p—CME—EDDP Immunogen

1-Ethyl-3-(3-dimethylaminopropyl)carbodiimide (EDC) (8.63 mg. 45 μmoles) and N-hydroxysuccinimide (NHS) (5.18 mg, 45 μmoles) were added with stirring to p—CME—EDDP (3.50 mg 7.5 μmoles) in 1 mL DMF. After 2 hours, 1 niL of phosphate buffer (100 mM, pH=7) was added, followed by keyhole limpet hemocyanin (KLH) (15 mg) in 1.5 mL of phosphate buffer (83 mM, pH=7.2, 0.9 M NaCl). After stirring for 5 hours, the mixture was dialyzed against 800 mL phosphate buffer (10 mM, pH=7, 150 mM NaCl) and 200 mL DMF. After 12 hours, the buffer was replaced. After an additional 12 hours, this buffer was replaced with 2 L of phosphate buffer (10 mM, pH=7, 150 mM NaCl) which was again replaced after another 12 hours. Twelve hours after the last buffer replacement, the immunogen was transferred to a vial and stored at −80° C. until used.

Preparation of KLH-2-IT—p—MEA—CME—EDDP Immunogen

2-Iminothiolane (2-IT) (2.06 mg, 15 μmoles) and 3.5 mL of phosphate buffer (100 mM, pH=8) were added to KLH (15 mg) in 1.5 mL of phosphate buffer (83 mM, pH=7.2, 0.9 M NaCl) with stirring. After 75 min, the mixture was split into two equal portions and each portion was desalted with a PD-10 pre-packed SEPHADEX™ G-25 ion exchange column (Pharmacia, Inc.) pre-equilibrated with phosphate buffer (100 mM, pH=8) to remove excess 2-IT. The eluant was added to p—MEA—CME—EDDP (1.77 mg, 3 μmoles) in 1.5 mL DMF. After stirring for 5 hours, the mixture was dialyzed against 800 mL phosphate buffer (10 mM, pH=7, 150 mM NaCl) and 200 mL DMF. After 12 hours, the buffer was replaced. After an additional 12 hours this buffer was replaced with 2 L of phosphate buffer (10 mM, pH=7, 150 mM NaCl), which was again replaced after another 12 hours. Twelve hours after the last buffer replacement, the immunogen was transferred to a vial and stored at −80° C. until used.

Conjugation of p—MEA—CME—EDDP to the enzyme donor ED28

A solution of desalted ED28 (1 mg, 102 nmol) in 234 μl phosphate buffer (100 mM, pH=7) was added with stirring to a solution of p—MEA—CME—EDDP (361 μg 610 nmol) in 180 μl DMF. After standing at RT for 1 hour, 586 μl of 20 mM TFA in water was added and the mixture was desalted on a PD-10 column pre-equilibrated with 20 mM TFA in water. The eluant (1.5 mL) was injected in a 10 mL loop and purified by HPLC (C4 1×25 cm, 0 min, 100% A; 0.1–20 min, 25–45% B; flow rate=4 mL/min; 280 nm). The total volume of eluant was 4.55 mL. The yield was 684 μg (61%) as determined by UV absorbance at 280 nm ($\epsilon_{280}$= 22,080). This solution was stored at −80° C. until further use.

Example 4

Development of EDDP-specific monoclonal antibodies and immunoassays

Immunization and hybridoma production

Monoclonal antibodies specific for EDDP were obtained using the immunogen KLH—p—CME—EDDP or alternatively KLH-2-IT—p—MEA—CME—EDDP. A priming injection and two booster injections were given using the same immunogen for each mouse. A total of 16 mice were immunized. The mice were bled, and each serum were assayed in a 96-well plate immunoassay. The assay used was a cloned enzyme donor immunoassay method, using ED28-p—MEA—CME—EDDP, prepared as in Example 3. Results are shown in Table 1:

TABLE 1

| | Immunoassay of Mouse Sera | | | |
|---|---|---|---|---|
| | | Modulation | Relative methadone cross-reactivity | |
| Immunogen | Average Titer | with free EDDP | range | average |
| KLH-p-CME-EDDP (No Linker) | 1:2500 | 62% ± 5% | 0–9% | 2% |
| KLH-2-IT-p-MEA-CME-EDDP (MEA linker) | 1:1300 | 59% ± 2% | 0–31% | 17% |

Titration results showed very good titer, 89–90% inhibition, and about 60% modulation with 10 X cut-off concentration. These results indicate that both immunogens work well to elicit a strong and specific response.

A mouse from the zero-linker group was chosen as the source of immunocompetent cells for the first fusion because of a slightly higher titer and lower average cross-reactivity with methadone. The parental myeloma used for all fusions was P3X63-Ag8.653, purchased through the American Type Culture Collection (ATCC). At the time of fusion, the spleen of the donor mouse was moderately enlarged. The first fusion produced 179 clones that strongly bound the EDDP conjugate (>60% inhibition) in a 96-well assay. Forty-four of these were retained on the basis of good modulation with EDDP and low cross-reactivity to methadone. A second fusion was performed in a similar fashion, from which 72 initial EDDP-binding positive clones were identified, of which 18 were retained. Culture supernatants from retained lines were grown to provide antibody samples for instrumentation analysis.

Assay development and antibody selection

Prototype imnunoassays for EDDP were developed using the cloned enzyme donor immunoassay technology described in U.S. Pat. No. 4,708,929. These assays were used to identify particular monoclonal antibodies with acceptable combinations of inhibition, titer, modulation, and low cross-reactivity.

Assays were performed as follows: Three µL of calibrator, control, or urine sample were automatically pipetted into the cuvette of a Boehringer Mannheim/Hitachi 717 Automated Analyzer, followed by 130 µL of Reagent 1 containing the β-galactosidase enzyme acceptor EA22 (1.7 g/L), a monoclonal antibody to EDDP (varying concentration), 0.5% (vol/vol) fetal bovine serum, and 10 mM magnesium acetate in assay buffer at a final pH of 6.9. The assay buffer was 0.4 M NaCl, 0.1 M 1,4-piperazinediethanesulfonic acid, 10 mM ethylene glycol-bis-(β-aminoethyl ether) N,N,N',N'-tetraacetic acid and 26 mM $NaN_3$. This mixture was incubated at 37° C. for 5 minutes, followed by addition of 130 µL Reagent 2. Reagent 2 contained the enzyme donor conjugate ED28-p—MEA—CME—EDDP, 2 mg/mL of the substrate chlorophenol-red-β-D-galactopyranoside, 2 mg/mL pepsin-fragmented bovine serum albumin (U.S. Pat. No. 5,212,081) and 5 mM ethylenediaminetetraacetic acid (EDTA) in assay buffer. Incubation continued at 37° C., and absorbance measurements were taken at 12-second intervals beginning 4 minutes after adding Reagent 2. The analyzer automatically measures the rate of change of absorbance at 570 nm, corrected for background absorbance at 660 nm.

The concentration of each antibody in the Reagent 1 formulation was varied to yield a standard curve exhibiting optimum response near the concentration of 100 ng EDDP/mL. The concentration of EDDP in a control or unknown sample can be estimated by comparing the rate of change of absorbance with the control or unknown sample with the rates of the calibrators. In normal use, the rate obtained for an unknown urine sample would be compared to the rate obtained for 100 ng EDDP/mL calibrator, termed the "cut-off" calibrator. Sample exhibiting rates above that of the cut-off calibrator are considered positive for EDDP, while those with rates below that of the cut-off calibrator are considered negative.

Antibody clones retained from the initial screening were tested for a combination of inhibition, titer, modulation, and low cross-reactivity, and a number were selected for further analysis.

A key goal of the assay was to achieve maximum discrimination between EDDP and methadone. Cross-reactivity to methadone was determined by testing samples containing various concentrations of methadone, and determining the concentration of methadone in urine which would give a rate equal to that of the cut-off EDDP calibrator (100 ng EDDP/mL). Cross-reactivity is determined by dividing this concentration of methadone by 100 ng/mL, and multiplying by 100%. Methadone cross-reactivities measured for several monoclonal antibodies to EDDP are as follows:

TABLE 2

Cross-reactivity of Monoclonal antibodies to EDDP

| Antibody | Relative cross reactivity to Methadone | Relative cross-reactivity to EMDP |
|---|---|---|
| 6A9 | 0.47% | — |
| 14C4 | 0.37% | — |
| 15E11 | 0.61% | — |
| 5B12 | 0.26% | 1.5% |
| 14G4 | 0.03% | 0.01% |
| 21G7 | 0.34% | 1.5% |
| 2C11 | — | 1.5% |
| 9H3 | — | 0.1% |
| 13A6 | — | 1.5% |

Five monoclonal antibodies were tested with a panel of about 50 compounds that were either licensed pharmaceuticals or potential substances of abuse, at levels that were high relative to the concentration likely to occur in test samples. Compounds showing reaction rates above the EDDP cut-off sample were retested in a dilution series. Results are shown in the next Table. Levels not marked were negative.

TABLE 3

Cross-reactivity of Monoclonal antibodies to EDDP

| Compound | | Monoclonal antibody | | | | |
|---|---|---|---|---|---|---|
| | | 5B12 | 6A9 | 14C4 | 14G4 | 21G7 |
| Pentazocine | 2.17 mg/mL | | | + | + | |
| | 1:10 | | | + | | |
| | 1:100 | | | | | |
| | 1:1000 | | | | | |
| Phencyclidine | 2.33 mg/mL | + | + | | + | + |
| | 1:10 | + | | | | + |
| | 1:100 | | | | | |
| | 1:1000 | | | | | |
| Loperamine | 1.46 mg/mL | | | + | | |
| | 1:10 | | | | | |
| | 1:100 | | | | | |
| | 1:1000 | | | | | |
| 2-OH Imipramine | 127 µg/mL | | | | | |
| | 1:10 | | | | | |
| | 1:100 | | | | | |
| | 1:1000 | | | | | |
| Dextromethorphan | 1.83 mg/mL | | | + | + | |
| | 1:10 | | | | | |
| | 1:100 | | | | | |
| | 1:1000 | | | | | |
| alpha-Methadol | 1.57 mg/mL | + | + | + | | + |
| | 1:10 | | + | | | |
| | 1:100 | | | | | |
| | 1:1000 | | | | | |
| d-Methamphetamine | 3.33 mg/mL | + | | | | + |
| | 1:10 | | | | | |
| | 1:100 | | | | | |
| | 1:1000 | | | | | |
| Norpropoxyphene | 560 µg/mL | | | | | |
| | 1:10 | | | | | |
| | 1:100 | | | | | |
| | 1:1000 | | | | | |
| Propoxyphene | 2.53 mg/mL | | | + | + | |
| | 1:10 | | | | | |
| | 1:100 | | | | | |
| | 1:1000 | | | | | |

Figure 10A:
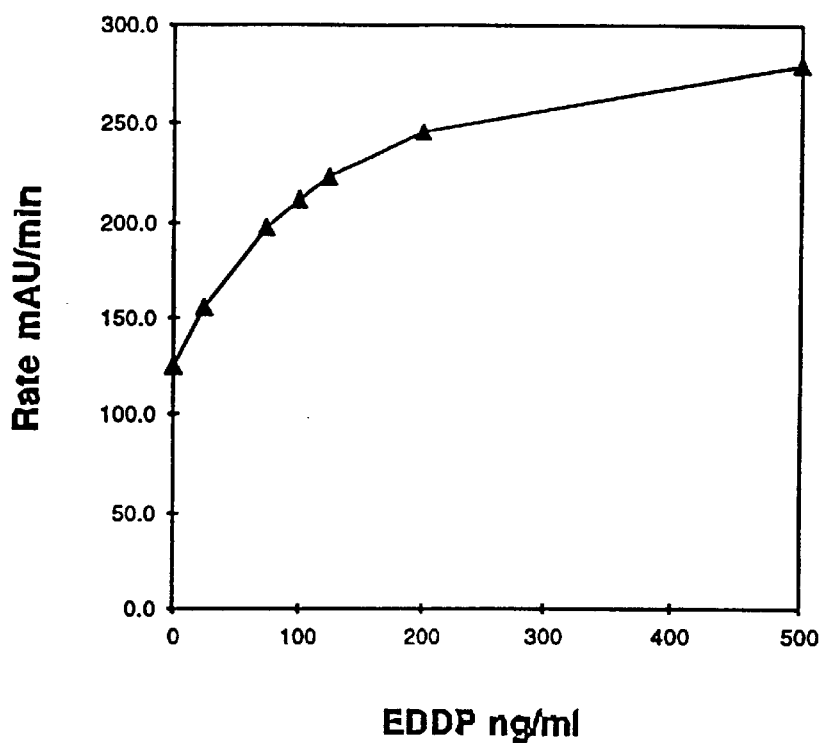
FIG. 10 is a line graph showing a cloned enzyme donor immunoassay EDDP immunoassay calibration curve, using the EDDP-specific monoclonal antibodies designated 14C4 (Panel A) and 14G4 (Panel B).
Figure 10B:
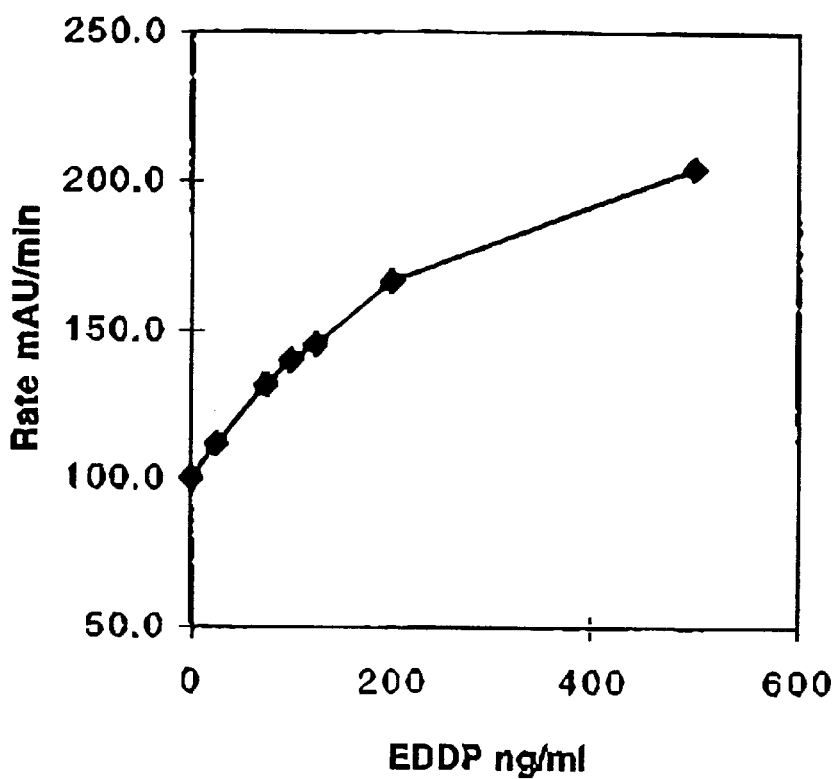

FIG. 10 shows the cloned enzyme donor immunoassay standard curves for monoclonal antibody 14C4 (Panel A) and 14G4 (Panel B). The 14G4 standard curve shows an inhibition of 65.1% over the open reaction rate of 285.6 mAU/min, a saturation at 100 ng/mL of 21.4%, and a modulation at 100 ng/mL of 28.5%.

Testing of biological samples

Prototype EDDP assays using various monoclonal antibodies to EDDP were evaluated for specificity using urine samples known to be free of methadone and other drugs, and for sensitivity using samples from subjects on methadone maintenance and containing known concentrations of methadone. Methadone levels were determined independently using the CEDIA® DAU methadone assay kit which is commercially available. Results for several monoclonal antibodies are summarized in the next Table.

TABLE 4

Assay results using biological test samples

| | Samples established by immunoassay to be METHADONE-NEGATIVE | | Samples established by immunoassay to be METHADONE-POSITIVE | |
|---|---|---|---|---|
| Antibody | EDDP negative | EDDP positive | EDDP negative | EDDP positive |
| 5B12 | 46 | 0 | 1 | 109 |
| 6A9 | 45 | 1 | 0 | 66 |
| 14C4 | 45 | 1 | 0 | 66 |
| 14G4 | 46 | 0 | 1 | 109 |

Samples containing 300 ng/mL methadone by immunoassay were identified as positive for methadone; samples containing less than this amount were considered negative.

Twenty-four samples which tested positive by the EDDP immunoassay method were further evaluated for EDDP by gas chromatography/mass spectrometry (GC/MS). All 24 samples were confirmed to contain EDDP by GC/MS. The one sample testing positive for EDDP in the methadone-negative group was confirmed by GC/MS to be negative for methadone but having >100 ng/mL EDDP. In addition, 50 urine samples known to be opiate positive were tested in the EDDP assay using antibody 14G4. Only one tested positive at the cut-off level of >100 ng/mL EDDP, and was vindicated as containing methadone with trace amounts of EDDP.

Monoclonal antibody 14G4 had the following characteristics: Of 110 methadone-positive samples, 109 tested positive for EDDP, giving a sensitivity of 99.1%. Specificity testing using 382 EDDP negative samples was 100%. Average cross-reactivity for methadone at 1000 μg/mL: 0.028%; at 100 μg/mL: 0.026%. The following drug-positive samples were also tested using antibody 14G4: propoxyphene (n=46), cocaine (n=50), opiates (n=49), amphetamines (n=91), barbiturates (n=48), PCP (n=50), benzodiazepines (n=48). None tested positive for EDDP.

What is claimed as the invention is:

1. A compound of the formula:

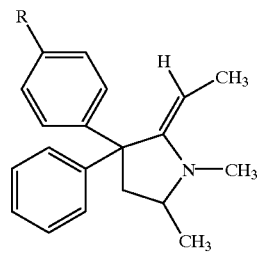

and salts thereof, wherein R comprises a poly(amino acid) attached through p—CO—L— where L is a bond or a diradical linker group.

2. A compound of the formula:

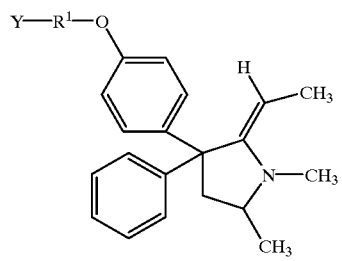

and salts thereof,
wherein $R^1$ is a hydrocarbyl diradical having 1–10 carbon atoms and
Y is
—CO—L—Q, wherein Q is a poly(amino acid) and L is a bond or a diradical linker group.

3. The compound of claim 2, wherein $R^1$ is a linear or branched alkyl diradical.

4. The compound of claim 2, wherein L is

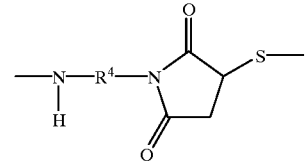

wherein $R^4$ is a hydrocarbyl diradical of 1–20 carbon atoms.

5. The compound of claim 2, wherein L is a bond and Y is —CO—Q.

6. The compound of claim 2, wherein $R^1$ is —$(CH_2)_m$— and m is 1 to 10.

7. The compound of claim 2, wherein $R^1$ is —$CH_2$—.

8. The compound of claim 4, wherein $R^4$ is —$(CH_2)_n$— and n is 1 to 10.

9. The compound of claim 4, wherein $R^4$ is —$CH_2CH_2$—.

10. The compound of claim 2, wherein Q is an immunogenic poly(amino acid).

11. The compound of claim 2, wherein Q is keyhole limpet hemocyanin (KLH) or thiolated KLH.

12. The compound of claim 2, wherein Q comprises an enzyme or a portion thereof.

13. The compound of claim 2, wherein Q is an enzyme donor polypeptide.

14. The compound of claim 13, wherein the enzyme donor polypeptide is a β-galactosidase polypeptide.

15. An antibody raised against a compound according to claim 2 and specific for the compound 2-ethylidene-1,5-dimethyl-3,3-diphenylpyrrolidone (EDDP).

16. An antibody raised against a compound according to claim 4 and specific for EDDP.

17. An antibody specific for EDDP and having a cross-reactivity with methadone of less than 2.0%.

18. The antibody of claim 15, having a cross-reactivity with methadone of less than 0.5%.

19. The antibody of claim 15, having a cross-reactivity with methadone of less than 0.1%.

20. An antibody specific for EDDP and having a cross-reactivity with the compound 2-ethyl-5-methyl-3,3-diphenyl-1-pyrroline (EMDP) of less than 1.0%.

21. A method for detecting EDDP in a sample, comprising the steps of:

a) combining the sample with the antibody of claim 15 under conditions that permit formation of a stable EDDP-antibody complex; and b) detecting any EDDP-antibody complex formed in step a).

22. The method of claim 21, comprising quantitating any EDDP-antibody complex formed in step a).

23. The method of claim 21, which is a competition assay method.

24. The method of claim 21, further comprising the steps of:

i) contacting the antibody with a labeled analog of EDDP under conditions that permit formation of a stable analog-antibody complex; and ii) separating any analog not forming a complex in step i).

25. The method of claim 21, which is a homogeneous assay method.

26. The method of claim 21, which is a cloned enzyme donor immunoassay method.

27. The method of claim 21, comprising the steps of:

i) combining the sample with:
   said antibody,
   an enzyme donor polypeptide conjugate according to the compound of claim 3,
   an enzyme acceptor polypeptide wherein said enzyme acceptor polypeptide capable of forming with said enzyme donor polypeptide conjugate an active enzyme complex in the absence of an antibody to EDDP, and
   a substrate capable of being transformed by the active enzyme complex into a product; and ii) measuring the rate of product formation.

28. The method of claim 27, wherein the active enzyme complex has β-galactosidase activity.

29. A method for generating an antibody specific for EDDP, comprising immunizing a mammal or contacting an immunocompetent cell or virus with the compound of claim 11.

30. A diagnostic kit for measuring EDDP in a sample, comprising the antibody of claim 15 in suitable packaging.

31. A diagnostic kit for measuring EDDP in a sample, comprising the compound of claim 12 in suitable packaging.

32. A method for making a diagnostic kit for measuring EDDP in a sample, comprising packaging the antibody of claim 15.

33. A method for making a diagnostic kit for measuring EDDP in a sample, comprising packaging the compound of claim 1.

34. An antibody to the methadone metabolite EDDP having a crossreactivity with methadone of less than 0.5%.

35. An antibody to the methadone metabolite EDDP having a crossreactivity with methadone of less than 0.1%.

* * * * *

UNITED STATES PATENT AND TRADEMARK OFFICE
CERTIFICATE OF CORRECTION

PATENT NO. : 6,140,137
DATED : October 31, 2000
INVENTOR(S) : Sigler et al.

It is certified that error appears in the above-identified patent and that said Letters Patent is hereby corrected as shown below:

Column 1,
Line 28, reads "herein abbreviated as EDDP)" and should read -- (herein abbreviated as EDDP) --.

Column 2,
Line 18, reads "I-chlorobutane" and should read -- 1-chlorobutane --.

Column 6,
Line 61, reads "FIG. 6,," and should read -- FIG. 6, --.

Column 8,
Line 54, reads "alkyi" and should read -- alkyl --.

Column 9,
Line 11, reads "arnide" and should read -- amide --.
Line 49, reads "thereof Linear or" and should read -- thereof. Linear --.

Column 17,
Line 26, reads "-p-methoxyphenyl)-" and should read -- -(methoxyphenyl)- --.
Line 31, reads "THE (30 mL)." and should read -- THF (30 mL). --.
Line 62, reads "trichloroethylchlorofornate" and should read
-- trichloroethylchloroformate --.

Column 18,
Line 61, reads "2-ethyl-1.5-dimethyl" and should read -- 2-ethyl-1,5-dimethyl --.
Line 63, reads "(-hydroxyphenyl)" and should read -- (p-hydroxyphenyl) --.

Column 19,
Line 1, reads "IM boron" and should read -- 1M boron --.
Line 17, reads "chlorofoinlmethanol" and should read -- chloroform/methanol --.
Line 29, reads "sulfuiric" and should read -- sulfuric --.
Line 31, reads "sulfturic" and should read -- sulfuric --.
Line 52, reads "finnel" and should read -- funnel --.

Column 20,
Line 48, reads "(ITA)" and should read -- (TFA) --.

Column 21,
Line 33, reads "1 niL" and should read -- 1mL --.

UNITED STATES PATENT AND TRADEMARK OFFICE
CERTIFICATE OF CORRECTION

PATENT NO. : 6,140,137
DATED : October 31, 2000
INVENTOR(S) : Sigler et al.

It is certified that error appears in the above-identified patent and that said Letters Patent is hereby corrected as shown below:

Column 22,
Line 18, reads "586,$\mu$l of" and should read -- 586$\mu$l of --.

Column 24,
Table 3, plus sign for alpha-Methadol 1:10 is under 5B12 column and should be under 6A9 column.

Signed and Sealed this

Thirteenth Day of November, 2001

Attest:

*Nicholas P. Godici*

NICHOLAS P. GODICI
*Attesting Officer*    *Acting Director of the United States Patent and Trademark Office*